United States Patent
Aparin et al.

(10) Patent No.: US 11,052,142 B2
(45) Date of Patent: Jul. 6, 2021

(54) MODIFIED ENDOTOXIC BACTERIA LIPOPOLYSACCHARIDE (VARIANTS), COMBINATION OF MODIFIED LIPOPOLYSACCHARIDES (VARIANTS) AND, CONTAINING SAME, A VACCINE (VARIANTS) AND A PHARMACEUTICAL COMPOSITION (VARIANTS)

(71) Applicants: Petr Gennadievich Aparin, Moscow (RU); Vyacheslav Leonidovich Lvov, Moscow (RU); Stanislava Ivanovna Elkina, Moscow (RU); Marina Eduardovna Golovina, Moscow (RU)

(72) Inventors: Petr Gennadievich Aparin, Moscow (RU); Vyacheslav Leonidovich Lvov, Moscow (RU); Stanislava Ivanovna Elkina, Moscow (RU); Marina Eduardovna Golovina, Moscow (RU); Vladimir Alekseyevich Ledov, g. Klimovsk (RU); Anna Aleksandrovna Markina, Moscow (RU); Maria Evgen'evna Shekht, Moscow (RU)

(73) Assignees: Petr G. Aparin, Moscow (RU); Vyacheslav L. Lvov, Moscow (RU); Stanislava I. Elkina, Moscow (RU); Marina E. Golovina, Moscow (RU)

(*) Notice: Subject to any disclaimer, the term of this patent is extended or adjusted under 35 U.S.C. 154(b) by 0 days.

(21) Appl. No.: 15/454,526

(22) Filed: Mar. 9, 2017

(65) Prior Publication Data
US 2018/0043004 A1 Feb. 15, 2018

Related U.S. Application Data

(63) Continuation-in-part of application No. 14/895,894, filed as application No. PCT/RU2013/000456 on Jun. 4, 2013, now abandoned.

(51) Int. Cl.
| | |
|---|---|
| A61K 39/108 | (2006.01) |
| A61K 39/112 | (2006.01) |
| C08B 37/00 | (2006.01) |
| A61K 39/02 | (2006.01) |
| A61K 39/00 | (2006.01) |

(52) U.S. Cl.
CPC ........ *A61K 39/0258* (2013.01); *A61K 39/025* (2013.01); *A61K 39/0266* (2013.01); *A61K 39/0275* (2013.01); *A61K 39/0283* (2013.01); *C08B 37/006* (2013.01); *A61K 2039/57* (2013.01); *A61K 2039/6037* (2013.01); *A61K 2039/62* (2013.01); *Y02A 50/30* (2018.01)

(58) Field of Classification Search
None
See application file for complete search history.

(56) References Cited

U.S. PATENT DOCUMENTS

| | | |
|---|---|---|
| 4,912,094 A | 3/1990 | Myers et al. |
| 4,929,604 A | 5/1990 | Munford et al. |
| 5,005,099 A | 4/1991 | Perryman et al. |
| 5,482,807 A | 1/1996 | Aoki et al. |
| 7,005,129 B1 | 2/2006 | Kpicella et al. |
| 7,553,490 B2 | 6/2009 | Szu et al. |
| 7,622,128 B2 | 11/2009 | Darveau et al. |
| 8,048,433 B2 | 11/2011 | Tommassen et al. |
| 2005/0147624 A1* | 7/2005 | Jennings .............. A61K 47/646 424/234.1 |
| 2005/0271675 A1 | 12/2005 | Schneerson et al. |
| 2009/0285854 A1* | 11/2009 | Contorni .............. A61K 39/145 424/209.1 |
| 2013/0203980 A1 | 8/2013 | Aparin et al. |

FOREIGN PATENT DOCUMENTS

| | | | | |
|---|---|---|---|---|
| RU | 2154068 C2 * | 8/2000 | ............. | C07H 13/06 |
| WO | WO-9719688 A1 * | 6/1997 | ......... | A61K 39/0275 |
| WO | WO-2007050606 A2 * | 5/2007 | ........... | A61K 39/025 |

OTHER PUBLICATIONS

Pacielloetal (PNAS (110:E4345-E4354; first published Oct. 28, 2013).*
D'Hauteville et al (J. Immunology 2002; 168:5240-5251).*
Caroff M., Novikov A. (2019) LPS Structure, Function, and Heterogeneity. In: Williams K. (eds) Endotoxin Detection and Control in Pharma, Limulus, and Mammalian Systems. Springer, Cham.*
International Search Report dated Mar. 6, 2014, for corresponding International Patent Application No. PCT/RU2013/000456.
Written Opinion dated Mar. 6, 2014, for corresponding International Patent Application No. PCT/RU2013/000456.

(Continued)

*Primary Examiner* — Oluwatosin A Ogunbiyi
(74) *Attorney, Agent, or Firm* — Pergament & Cepeda LLP; Milagros A. Cepeda; Edward D. Pergament

(57) ABSTRACT

For the first time individual (free from impurities of penta- and hexa-acetylated derivatives) di-, tri- and tetra-acetylated S-LPS of endotoxic bacteria and combinations thereof were obtained and their immunobiological, physical-chemical and chemical-pharmaceutical properties were studied.

For the first time the principal possibility of their clinical application was directly demonstrated as vaccines and pharmaceutical compositions containing the modified S-LPS individual as monocomponent or combinations thereof as two and three component active substance, respectively.

The modified S-LPS and combinations thereof have high safety profile and provide low pyrogenicity and high immunogenicity. Developed on their basis vaccines and pharmaceutical compositions demonstrate anti-shock activity, high efficiency and specificity, broad-spectrum action and also good chemical-pharmaceutical parameters.

58 Claims, 11 Drawing Sheets

(56) References Cited

OTHER PUBLICATIONS

International Preliminary Report on Patentability dated Dec. 8, 2015, for corresponding International Patent Application No. PCT/RU2013/000456.

Rezania et al., "Extraction, Purification and Characterization of Lipopolysaccharide from *Escherichia coli* and *Salmonella typhi*", Avicenna J Med Biotech, Jan.-Mar. 2011, pp. 3 to 9, vol. 3—issue No. 1.

Pavliakova et al., "Clostridium difficile Recombinant Toxin a Repeating Units as a Carrier Protein for Conjugate Vaccines: Studies of Pneumococcal Type 14, *Escherichia coli* K1, and Shigella flexneri Type 2a Polysaccharides in Mice", Infection and Immunity, Apr. 2000, pp. 2161 to 2166, vol. 68—issue No. 4, American Society for Microbiology.

Alexander and Rietschel, "Bacterial lipopolysaccharides and innate immunity", Journal of Endotoxin Research, 2001, pp. 167 to 202, vol 7—Issue No. 3, W S. Maney & Son Ltd.

Bainbridge and Darveau, "Porphyromonas gingivalis lipopolysaccharide: an unusual pattern recognition receptor ligand for the innate host defense system", Acta Odontol Scand, 2001, pp. 131 to 138, vol. 59.

Brandenbrg et al., "Physicochemical characteristics of triacyl lipid a partial structure OM-174 in relation to biological activity", Eur. J. Biochem., 2000, pp. 3370 to 3377, vol. 267, Feb. 2000.

Darveau et al., "Ability of Bacteria Associated with Chronic Inflammatory Disease to Stimulate E-Selectin Expression and Promote Neutrophil Adhesion", Infection and Immunity, Apr. 1995, pp. 1311 to 1317, vol. 63—Issue No. 4, American Society for Microbiology.

Konadu et al., "Synthesis, Characterization, and Immunological Properties in Mice of Conjugates Composed of Detoxified Lipopolysaccharide of *Salmonella paratyphi* A Bound to Tetanus Toxoid, with Emphasis on the Role of O Acetyls", Infection and Immunity, Jul. 1996, pp. 2709 to 2715, vol. 64—Issue No. 7, American Society for Microbiology.

\* cited by examiner

MODIFIED ENDOTOXIC BACTERIA LIPOPOLYSACCHARIDE (VARIANTS), COMBINATION OF MODIFIED LIPOPOLYSACCHARIDES (VARIANTS) AND, CONTAINING SAME, A VACCINE (VARIANTS) AND A PHARMACEUTICAL COMPOSITION (VARIANTS)

This application is a Continuation-in-Part of U.S. patent application Ser. No. 14/895,894, filed Dec. 3, 2015, which is a National Stage Application under 35 U.S.C. § 371 of PCT International Application No. PCT/RU2013/000456, filed Jun. 4, 2013, all of which are hereby incorporated by references in their entireties.

TECHNICAL FIELD

The invention relates to the clinical immunology and pharmacology, in particular to modified lipopolysaccharides of endotoxic bacteria, specifically *Salmonella, Escherichia, Shigella, Bordetella, Haemophilus, Neisseria, Campylobacter, Vibrio, Klebsiella, Chlamydia, Corynebacterium* and their combinations, along with vaccines and pharmaceutical compositions comprising them.

PRIOR ART

Lipopolysaccharides (LPS) are endotoxins of gram-negative bacteria and consist of polysaccharide (O-PS) and lipid components.

The lipid component, which is also referred to as lipid A, determines the endotoxic properties of lipopolysaccharides (Rietschel E. T., Kirikae T., Schade F. U., Ulmer A. J., Holst O., Brade H., Schmidt G., Mamat U., Grimmecke H. D., Kusumoto S. et al. The chemical structure of bacterial endotoxin in relation to bioactivity. Immunobiology, 1993, April; 187(3-5): 169-190).

Polysaccharide component of LPS is a O-specific polysaccharide—O-PS composed of repeating oligosaccharide units and is connected to core oligosaccharide, which in turn is connected to lipid A. LPS composed of all three structural parts, O-PS, core and lipid A, are called S-LPS because they are characteristic of the «smooth» colonies of microorganisms.

O-PS is absent in the LPS structure of some bacteria, including pathogenic bacteria. These microorganisms form rough colonies in many cases and produce low molecular LPS, so called R-LPS, which contain only core oligosaccharide linked to lipid A. It has been shown that the unique structure of O-PS determines the immunospecificity of S-LPS and of the whole microorganism as a consequence, and in many cases S-LPS-specific antibodies induced in the host in response to S-LPS play a key role against bacterial infection and exhibit high protective capacity.

However it is well known that, besides the ability to activate the adaptive immunity, LPS even in minimal doses are very endotoxic. In response to appearance of significant amounts of LPS in a macro-organism, there occurs a state of endotoxic shock, which rules out the use of LPS as components of vaccines and therapeutic drugs.

Endotoxic component of LPS—lipid A is usually disaccharide composed of two phosphorylated glucosamine residues, each of which is N- and O-acetylated (at the 3 and 3' positions) by four 3-hydroxymyristic acid residues (HMA) which are called primary. Two other non-hydroxylated higher fatty acid residues (typically lauric and myristic acids) 0-acetylate two of the abovementioned HMA residues, which are called secondary. Therefore so called «classic» lipid A consists of six (four primary and two secondary) higher fatty acid residues (Knirel Yu. A., Valvano M. A. Bacterial Lipopolysaccharides. Structure, Chemical Synthesis, Biogenesis and Interaction with Host Cells. Springer Wien New York, 2011, 440 PP.).

It is believed that LPS of gram-negative microorganisms which does not contain «classic» lipid A with six higher fatty acid residues, but which contain smaller number of fatty acid residues in lipid A, have reduced level of endotoxicity.

It is believed that reduction of endotoxicity of S-LPS to clinically acceptable levels with retention of their ability to induce specific protective antibody to polysaccharide epitopes leads to principal possibility of using low endotoxic modified S-LPS of endotoxic bacteria, actual infectious agents, as immunoprophylactic vaccines and medicinal drugs.

The studies of transformations of endotoxic LPS containing «classic» lipid A to lower endotoxic derivatives prepared by methods of chemical, enzymatic and genetic detoxification have started over 20 years ago.

According to U.S. Pat. No. 4,912,094, penta-acetylated derivative of R-LPS (composed of lipid A with five fatty acid residues) of endotoxic bacteria—*Salmonella enterica* sv *minnesota* and *Escherichia coli*, were obtained by controlled alkaline hydrolysis of LPS resulting in selective cleavage of O-hydroxymyristic acid, which is connected to reducing end of glucosamine at the 3 position by ester bond. At the same time, data for the reduction of endotoxicity of modified R-LPS were very limited; it was noted that the toxicity decreased only about 50 times in the chicken embryo toxicity test. Pharmaceutical tests of toxicity reduction for R-LPS (side reactions and pyrogenicity tests) were not carried out.

According to U.S. Pat. No. 6,482,807, penta-acetylated LPS with reduced endotoxicity was obtained by genetic engineering from genetically modified recombinant *Neisseria meningitidis* bacteria by blocking production of hexa-acetylated form of LPS in cell. However thus obtained LPS demonstrated insignificant endotoxicity reduction (only 100-fold decrease of endotoxicity was observed according to the test data for the in vitro TNF-α production). The modified strain was only 7 times different from the initial strain by decreasing activity in LAL-test. Pharmaceutical pyrogenic assay data of LPS product were not presented. The product was described as an adjuvant, not a vaccine antigen.

It is clear at the present time that penta-acetylated LPS of endotoxic bacteria retain essential level of endotoxicity in experimental animals and thus they cannot find clinical application as components of pharmaceutical preparations.

According to U.S. Pat. No. 4,929,604, derivatives of lipid component of LPS of endotoxic bacteria, primarily composed of primary residues of 3-hydroxymyristic acid were obtained with acyloxyacyl hydrolase by the method of selective enzymatic hydrolysis. However, removal of secondary fatty acid was incomplete and only 80-90% of secondary fatty acids were removed even by using maximum time period of enzymatic treatment. Thus the product of this enzymatic treatment is a mixture of tetra-acylated derivatives of LPS (including lipid A with four fatty acid residues) with unreacted penta- and hexa-acylated derivatives of LPS (including lipid A with five and six fatty acid residues, respectively) of *Escherichia* or *Haemophilus* or *Neisseria*. Furthermore immunobiological properties of the mixture of tetraacyl derivatives with penta- and hexa-acylated derivatives, but not pure tetra-acetylated derivatives of LPS, were studied. The study results were unsatisfactory: only 20-fold decrease in activity of the mixture of modified LPS was observed in the LAL-test in comparison with the initial LPS. The reduction of level of pyrogenicity was insignificant (only 2.5-3 times) calculated by thermal response index in the rabbit pyrogenicity test. In the patent text the assessment of decrease in skin sensitization effect of maximum deacetylated LPS under study in Schwartzman reaction was described in a contradictory way (decreasing from 10- to 100-times).

The mixture of penta- and tetra-acetylated derivatives of R-LPS and S-LPS of endotoxic *H. influenzae* and *B. pertussis* bacteria was also prepared from genetically modified strains by transformation of their enzymatic systems (U.S. Pat. No. 7,005,129 B1; WO 2006065139 A2). However the obtained mixture of mutant LPS had high residual endotoxicity and cannot be used as potential immunogens for humans.

Thus the methods of enzymatic treatment described in patents leading to production of the mixture of tetra-, penta- and hexa-acylated derivatives of LPS of endotoxic bacteria do not result in significant endotoxicity reduction that prevents their clinical application as a component of pharmaceutical preparations.

Prior art shows that preparations of modified LPS of endotoxic bacteria which are penta-acylated derivatives or combination of tetra-, penta-, and hexaacetylated derivatives in no way meet clinical safety criteria. Apparently this is why authors of the abovementioned patents did not conduct standard studies of immunogenicity of preparations as candidate vaccines. The preparation of modified LPS was principally considered for use as immunostimulants and because of this reason the immunogenic study of the preparations and the evaluation of the immune response against O-antigen domain of LPS were not carried out.

Due to unsatisfactory safety level of abovementioned modified LPS, produced by inefficient deacetylation of lipid A, this line of research was practically abandoned. Therefore since the end of last century no patents have been obtained and no papers have been published dedicated to the preparation of other modified LPS and in particular modified S-LPS from actual endotoxic bacterial strains (genetically unmodified) and their application as a potential vaccines for administration to humans. The principal possibility of using di-, tri- and tetra-acetylated derivatives of LPS of endotoxic bacteria as vaccines was not in view of the researchers. This area has never previously been considered as the subject of targeted practical application by vaccinologists.

The studies in the field of design of clinically applicable vaccines have moved to another paradigm, notably the use of cleavage elements of S-LPS-O-PS, fragment of 0-PS-core with diglycosamine residues or lipid A obtained by full deacylation with hydrazine as specific antigen for conjugation with protein carriers. (U.S. Pat. No. 7,553,490; Konadu E., Shiloach J., Bryla D. A., Robbins J. B., Szu S. C. Synthesis, characterization and immunological properties in mice of conjugates composed of detoxified lipopolysaccharide of *Salmonella paratyphi* A bound to tetanus toxoid with emphasis on the role of O-acetyls. Infect. Immun., 1996, July, 64(7): 2709-15; Pavliakova D., Moncrief J. S., Lyerly D. M., Schiffman G., Bryla D. A., Robbins J. B., Schneerson R. *Clostridium difficile* recombinant toxin A repeating units as a carrier protein for conjugate vaccines: studies of pneumococcal type 14, *Escherichia coli* K1 and *Shigella flexneri* type 2a polysaccharides in mice. Infect. Immun., 2000, April, 68(4):2161-6).

Therefore, the prior art does not suggest the claimed modified lipopolysaccharides, pure di-, tri-, and tetra-acetylated derivatives of LPS of endotoxic bacteria, and their clinical application as direct vaccine drug preparations, either as S-LPS individually or combinations thereof as two- and three-component active substances.

Information about deacylated LPS of *Porphyromonas gingivalis* bacteria—component of oral cavity microflora is indirectly relevant to the claimed objects. According to U.S. Pat. No. 7,622,128, penta-, tetra-, tri-acetylated derivatives of *P. gingivalis* LPS were obtained and the principal possibility was demonstrated of using pentaacetylated and tetraacetylated derivatives as immunomodulators composed of the corresponding compositions. At the same time the data for characterizing their safety level and possibility of their clinical application are absent.

*P. gingivalis* produces LPS with fairly low endotoxicity and pyrogenicity (with 1000-fold decreasing ability to activate proinflammatory cytokines and with 100-fold decreasing toxicity in galactosamine model compared to LPS from endotoxic *E coli* bacteria), first of all it was explained by structural features of the lipid A.

*P. gingivalis* is agent of local low intensity infection of oral cavity and the use of its LPS as protective antigen against this infection requires development of special approaches in preventive vaccination. (Darveau R. P., Cunningham M. D., Bailey T., Seachord C., Ratcliffe K., Bainbridge B., Dietsch M., Page R. C., Aruffo A. Ability of bacteria associated with chronic inflammatory disease to stimulate E-selectin expression and promote neutrophil adhesion. Infect. Immun., 1995, April, 63(4):1311-7; Bainbridge B. and Darveau R. P. *Porphyromonas gingivalis* Lipopolysaccharide: an Unusual Pattern Recognition Receptor Ligand for the Innate Host Defense System. Acta. Odontol. Scand., 2001, 59:131-8).

It was shown that about half of fatty acids in LPS *P. gingivalis* lipid A had unusually branched structure and contains an odd number of carbon atoms, dramatically distinguishing this LPS from LPS of endotoxic bacteria containing «classic» lipid A.

The closest analogues of the claimed objects in the part of modified S-LPS of endotoxic bacteria are solely for formal reasons the technical solutions of U.S. Pat. No. 4,912,094 and WO 9514026 A1.

In unreasonably broad patent claims of these patents, the general structural formula is characterized by a large group of modified S-LPS, R-LPS and modified lipid A of endotoxic bacteria, while only penta-acetylated derivatives of R-LPS and lipids A of *S. enterica* sv *minnesota* and *E. coli* in the former case and tri-acetylated and tetra-acetylated derivatives of *E. coli*, *Haemophilis influenzae* and *Pseudomonas aeruginosa* lipid A in the latter case, was practically obtained and studied for immunobiological properties.

The data in U.S. Pat. No. 4,912,094 were discussed above, while information in WO 9514026 A1 is subject to discussion in details.

Tri-acetylated derivatives of lipid A of abovementioned bacteria were powerful inducers of a key mediator of endotoxin reaction—TNF-α in vivo, and also of another pro-inflammatory cytokine—IL-6 (data from analogue patent RU 2154068 C2). In the culture of PMN in vitro tri-acylated derivatives of lipid A induced even higher TNF-α production in comparison with LPS Westphal.

In this regard, the conclusions about low endotoxicity of preparations of modified lipid A based on its low activity in LAL-test (1000-fold decreasing) in the document WO 9514026 A1 and in the analogue patents are unfounded. The evaluation of endotoxicity of LPS is incomplete only on the basis of in vitro LAL-test based on gel-forming activity of Limulus protein, ignoring the test results in vivo, reflecting production of pro-inflammatory cytokines (plasma concentration, pyrogenicity, side reactions). There are no data on pyrogenicity level and thus on the safety of obtained products.

Subsequent author publications of indicated documents go to prove that tri- and tetra-acylated lipid A developed as component of anticancer immune drugs, having essential residual endotoxicity and safety level, are not acceptable as traditional vaccine drugs (Brandenburg K., Lindner B., Schromm A., Koch M. H. J., Bauer J., Merkli A., Zbaeren C., Davies J. G., Seydel U. Physicochemical characteristics of triacyl lipid A partial structure OM-174 in relation to biological activity. Eur. J. Biochem., 2000, v. 267, pp. 3370-7). Modified lipid A cannot be used as a vaccine (it does not contain O-PS bacteria antigen) and this is a problem in terms of using them as additional component-adjuvant because of absence of data supporting their low pyrogenicity.

In the light of the foregoing, there were absolutely unexpected results of the comparative study of the induction in vivo of pro-inflammatory cytokine and mediator of endotoxin reaction—TNF-α by tri-acetylated lipid A from *E. coli* OM-174 and thus di-, tri-, and tetra-acetylated endotoxic bacteria S-LPS, respectively, conducted by authors of the present application and described in Example 1.

In distinction to modified lipid A, corresponding modified S-LPS of endotoxic bacteria were poor inducers of endotoxic shock and exhibits low pyrogenicity and endotoxicity for laboratory animal and human subjects.

These original results introduce certain corrections in the generally accepted view of contribution of the polysaccharide component to immunobiological properties of S-LPS, and also allow to establish correlation between the extent of modification of LPS of endotoxic bacteria and optimal ratio of their safety and immunogenicity levels, which opens the perspectives of their clinical use.

DISCLOSURE OF THE INVENTION

The objectives of the claimed inventions are:
(i) preparation of pure individual (free from impurities of penta- and hexaacylated derivatives) modified S-LPS of endotoxic bacteria (di-, tri- and tetra-acylated derivatives) and combinations thereof;
(ii) development of vaccines and pharmaceutical compositions on the basis of indicated objects containing modified S-LPS as individual monocomponent or combinations thereof as two- and three-component active substance, respectively.

The technical results, provided by the claimed inventions, are:
(a) high safety level (there are no endotoxin reactions—chills, fever, tachycardia, increase in arterial blood pressure when individual modified S-LPS or combinations thereof were parenterally administered to volunteers in a single dose of up to 200 mcg);
(b) low pyrogenicity (1,000-10,000-fold decrease of pyrogenic dose of individual modified S-LPS and combinations thereof in the rabbit pyrogenicity test in comparison with classic LPS Westphal; slight, up to 37.6° C. temperature reaction when indicated products were parenterally administered to volunteers in a single dose of up to 200 mcg);
(c) anti-shock activity (pre-administration of individual modified S-LPS or combinations thereof provides 80% animal survival rate undergoing endotoxic shock induced by administration of lethal dose of endotoxin; moreover administration of indicated products provides the correction of septic shock and slows down the development of peritonitis for 18-30 hours);
(d) high efficiency and specificity (immunization of volunteers and experimental animals with individual modified S-LPS or combinations thereof determines the production of high levels of LPS-specific and O-antigen specific IgG, IgA, IgM; four-fold sero-conversion of antibodies and direct animal protection in experimental infection models);
(e) broad-spectrum action (development of combined multivalent vaccines containing individual modified S-LPS or their combinations on the basis of two or several serotypes);
(f) synergistic effect observed for the combinations of modified S-LPS with regard to pyrogenicity reduction and immunogenicity enhancement;
(g) good chemical-pharmaceutical characteristics of individual modified S-LPS as well as their combinations (thermostability, extended storage period, environmental resistance).

For the first time, individual (free from impurities of penta- and hexaacylated derivatives) di-, tri- and tetraacylated S-LPS of endotoxic bacteria and also combinations thereof were obtained and their immunobiological, physical-chemical, chemical-pharmaceutical properties were investigated.

To clarify the scope of claims with regard to sources of claimed objects we should define a notion of «endotoxic bacteria» of *Salmonella, Escherichia, Shigella, Bordetella, Haemophilus, Neisseria, Campylobacter, Vibrio, Klebsiella, Chlamydia, Corynebacterium* genera.

Such bacteria should be called strains of natural genetically unmodified, gram-negative bacteria obtained from patients with infectious diseases or other environmental sources which produce endotoxic agonistic form of LPS molecules, which are characterized by high toxicity and pyrogenicity in free or associated with cell forms and high degree of acylation of lipid A (penta- or hexaacylated). The course of infectious process induced by endotoxic strain of bacteria—active producer of endotoxic LPS, is burdened by apparent temperature reactions, fever and other signs of Systemic Inflammatory Response Syndrome (SIRS).

On the other hand, low-endotoxic, gram-negative, naturally occurring bacteria have 100-1000 times lower endotoxicity. So it requires 100-1000 times more cells of low-endotoxic bacteria (*Helicobacter pylori, P. gingivalis, Treponema pallidum*) compared with amount of endotoxic bacteria cell (*E. coli*) to achieve the similar level of activation of epithelial cells receptors, PMN, TNF-α, IL-6. (Darveau R. P., Cunningham M. D., Bailey T., Seachord C., Ratcliffe K., Bainbridge B., Dietsch M., Page R. C., Aruffo A. Ability of bacteria associated with chronic inflammatory disease to stimulate E-selectin expression and promote neutrophil adhesion. Infect. Immun., 1995, April, 63(4):1311-7).

Low-endotoxic bacteria are either virulent free or they cause low intensity, often subclinical forms of mucosal infections, that is why they are often called "invisible bacteria". LPS of low-endotoxic bacteria always has structural features which are responsible for their low endotoxicity-low degree of lipid A acylation (tri- or tetraacylation), dephosphorylated form of lipid A, unique fatty acid structure (Alexander C., Rietschel E. T. Bacterial lipopolysaccharides and innate immunity. J. Endotoxin Res., 2001, v. 7, pp. 167-202.).

Modified lipopolysaccharide (S-LPS) of endotoxic bacteria was obtained comprising: O-specific polysaccharide, consisting of one or more repeating units, core oligosaccharide and fully O-deacylated lipid A with two acyl residues.

The claimed lipopolysaccharide has no less than 85% purity (Example 2B), generates protection against *Salmonella, Escherichia, Shigella, Bordetella, Haemophilus, Neisseria, Campylobacter, Vibrio, Klebsiella, Chlamydia, Corynebacterium* and combinations thereof by inducing a synthesis of specific antibacterial IgG, IgA, IgM antibodies in mammals, including humans (Examples 2D, 3F), has anti-shock activity for septic and/or endotoxic shock and is the immune system response modulator in mammals, including humans (Examples 3F, 4C), and is apyrogenic for a rabbit in a dose of up to 100 mcg/kg in the rabbit pyrogenicity test (Example 2C).

Modified lipopolysaccharide (S-LPS) of endotoxic bacteria was obtained comprising: O-specific polysaccharide, consisting of one or more repeating units, core oligosaccharide and partially O-deacylated lipid A with three acyl residues.

The claimed lipopolysaccharide has no less than 80% purity (Example 2B), generates protection against *Salmonella, Escherichia, Shigella, Bordetella, Haemophilus, Neisseria, Campylobacter, Vibrio, Klebsiella, Chlamydia, Corynebacterium* and combinations thereof by inducing a synthesis of specific antibacterial IgG, IgA, IgM antibodies in mammals, including humans (Examples 2D, 3C, 3F), has anti-shock activity for septic and/or endotoxic shock (Examples 3D) and is the immune system response modulator in mammals, including humans, and is apyrogenic for a rabbit in a dose of up to 100 mcg/kg in the rabbit pyrogenicity test (Example 2C).

Modified lipopolysaccharide (S-LPS) of endotoxic bacteria was obtained comprising: O-specific polysaccharide consisting of one or more repeating units, core oligosaccharide, and partially O-deacylated lipid A with four acyl residues.

The claimed lipopolysaccharide has no less than 80% purity (Example 2B), generates protection against *Salmonella, Escherichia, Shigella, Bordetella, Haemophilus, Neisseria, Campylobacter, Vibrio, Klebsiella, Chlamydia, Corynebacterium* and combinations thereof by inducing a synthesis of specific antibacterial IgG, IgA, IgM antibodies in mammals, including humans (Example 2D), has anti-shock activity for septic and/or endotoxic shock and is the immune system response modulator in mammals, including humans, and is apyrogenic for a rabbit in a dose of up to 100 mcg/kg in the rabbit pyrogenicity test (Example 2C).

The combination of modified lipopolysaccharides (S-LPS) of endotoxic bacteria was obtained comprising diacylated and triacylated derivatives at any ratio. The claimed combination exhibits synergistic effect with regard to immunogenicity enhancement compared with diacylated lipopolysaccharide derivative (Example 2D), generates protection against *Salmonella, Escherichia, Shigella, Bordetella, Haemophilus, Neisseria, Campylobacter, Vibrio, Klebsiella, Chlamydia, Corynebacterium* and combinations thereof by inducing a synthesis of specific antibacterial IgG, IgA, IgM antibodies in mammals, including humans (Example 2D), has anti-shock activity for septic and/or endotoxic shock and is the immune system response modulator in mammals, including humans (Examples 3C), and is apyrogenic for a rabbit in a dose of up to 100 mcg/kg in the rabbit pyrogenicity test (Example 2C).

The combination of modified lipopolysaccharides (S-LPS) of endotoxic bacteria was obtained comprising diacylated and tetraacylated derivatives at any ratio. The claimed combination exhibits synergistic effect with regard to immunogenicity enhancement compared with di-acylated lipopolysaccharide derivative (Example 2D), generates protection against *Salmonella, Escherichia, Shigella, Bordetella, Haemophilus, Neisseria, Campylobacter, Vibrio, Klebsiella, Chlamydia, Corynebacterium* and combinations thereof by inducing a synthesis of specific antibacterial IgG, IgA, IgM antibodies in mammals, including humans (Example 2D), has anti-shock activity for septic and/or endotoxic shock and is the immune system response modulator in mammals, including humans (Examples 3C), and is apyrogenic for a rabbit in a dose of up to 100 mcg/kg in the rabbit pyrogenicity test (Example 2C).

The combination of modified lipopolysaccharides (S-LPS) of endotoxic bacteria was obtained comprising tri-acylated and tetra-acylated derivatives at any ratio. The claimed combination exhibits synergistic effect with regard to immunogenicity enhancement compared with tetra-acylated lipopolysaccharide derivative, generates protection against *Salmonella, Escherichia, Shigella, Bordetella, Haemophilus, Neisseria, Campylobacter, Vibrio, Klebsiella, Chlamydia, Corynebacterium* and combinations thereof by inducing a synthesis of specific antibacterial IgG, IgA, IgM antibodies in mammals, including humans (Example 2D), has anti-shock activity for septic and/or endotoxic shock and is the immune system response modulator in mammals, including humans, and is apyrogenic for a rabbit in a dose of up to 100 mcg/kg in the rabbit pyrogenicity test (Example 2C).

The combination of modified lipopolysaccharides (S-LPS) of endotoxic bacteria was obtained comprising di-acylated, tri-acylated and tetra-acylated derivatives at any ratio. The claimed combination exhibits synergistic effect with regard to immunogenicity enhancement compared with di-acyled and tri-acylated lipopolysaccharide derivatives (Example 2D, 3F), generates protection against *Salmonella, Escherichia, Shigella, Bordetella, Haemophilus, Neisseria, Campylobacter, Vibrio, Klebsiella, Chlamydia, Corynebacterium* and combinations thereof by inducing a synthesis of specific antibacterial IgG, IgA, IgM antibodies in mammals, including humans (Examples, 2D, 3F, 3C), has antishock activity for septic and/or endotoxic shock (Example 3D) and is the immune system response modulator in mammals, including humans (Examples 3F, 4B, 4C), and is apyrogenic for a rabbit in a dose of up to 100 mcg/kg in the rabbit pyrogenicity test (Example 2C).

Vaccine was developed for prophylaxis and/or treatment of infectious diseases caused by gram-negative bacteria.

The claimed vaccine comprises the preventive and/or therapeutically effective amount of the modified lipopolysaccharide (S-LPS) of endotoxic bacteria—its di-acylated or tri-acylated, or tetra-acylated derivative. The claimed vaccine generates protection against *Salmonella, Escherichia, Shigella, Bordetella, Haemophilus, Neisseria, Campylobacter, Vibrio, Klebsiella, Chlamydia, Corynebacterium* and combinations thereof by inducing a synthesis of specific antibacterial IgG, IgA, IgM antibodies in mammals, including humans (Examples 3C, 3F), and provides prophylaxis and/or correction of the course of septic and/or endotoxic shock (Example 3D). In the claimed vaccine the modified lipopolysaccharides are apyrogenic for a rabbit in a dose of up to 100 mcg/kg in the rabbit pyrogenicity test (Example 3B).

The claimed vaccine may comprise pharmaceutically acceptable additives, which may be pH stabilizers or preservatives, or adjuvants, or isotonizing agents, or combinations thereof (Example 3A). Moreover, the vaccine may comprise modified lipopolysaccharide in non-conjugated as well as in conjugated form. Meanwhile, the vaccine, comprised of the conjugated form of the lipopolysaccharide, additionally contains carrier protein, namely diphtheria toxoid or tetanus toxoid, or *P. aeruginosa* exoprotein A, or other proteins (Example 3H, 3I).

The claimed vaccine comprises the preventive and/or therapeutically effective amount of the combination of the modified lipopolysaccharides (S-LPS) of endotoxic bacteria—di-acylated and tri-acylated derivatives or di-acylated and tetra-acylated derivatives, or tri-acylated and tetra-acylated derivatives, or di-acylated, tri-acylated and tetra-acylated derivatives. The claimed vaccine generates protection against *Salmonella, Escherichia, Shigella, Bordetella, Haemophilus, Neisseria, Campylobacter, Vibrio, Klebsiella, Chlamydia, Corynebacterium* and combinations thereof by inducing a synthesis of specific antibacterial IgG, IgA, IgM antibodies in mammals, including humans (Examples 3C, 3F), and provides prophylaxis and/or correction of the course of septic and/or endotoxic shock (Example 3D). In the claimed vaccine combinations of the modified lipolysaccharides are apyrogenic for a rabbit in a dose of up to 100 mcg/kg in the rabbit pyrogenicity test (Example 3B).

The claimed vaccine may comprise pharmaceutically acceptable additives, which may be pH stabilizers or preservatives, or adjuvants, or isotonizing agents, or combinations thereof (Example 3A). Moreover, the vaccine may comprise modified lipopolysaccharide in non-conjugated as well as in conjugated form. Meanwhile, the vaccine, comprised of the conjugated form of the lipopolysaccharide, additionally contains carrier protein, namely diphtheria toxoid or tetanus toxoid, or *P. aeruginosa* exoprotein A, or other proteins (Example 3G).

It should be noted that the claimed vaccines on the basis of individual S-LPS and combinations thereof can simultaneously induce the broadest spectrum of antibodies to various antigen determinants of different domains of LPS molecule (O-PS, outer core, inner core), that can be considered as an important factor of an efficiency of protective immunity. In addition, the possibility of development of multivalent vaccine have been demonstrated in which each of monovaccine variants contain an antigen specific to the most epidemically significant strain of gram-negative bacteria (Example 3I).

The pharmaceutical composition was developed comprising the effective amount of the modified lipopolysaccharide (S-LPS) of endotoxic bacteria—its di-acylated or tri-acylated, or tetra-acylated derivative. The claimed pharmaceutical composition is the immune system response modulator in mammals, including humans (Example 4C); the modified lipopolysaccharide containing in its formulation is apyrogenic for a rabbit in a dose of up to 100 mcg/kg in the rabbit pyrogenicity test (Example 2C).

The claimed pharmaceutical composition may comprise pharmaceutically acceptable additives, which may be preservatives or stabilizers, or solvents, or combinations thereof.

The claimed pharmaceutical composition has a broad-spectrum pharmacological activity and notably exhibits effective therapeutic antiviral action against infection caused by influenza A H1N1 virus (Example 4B). Moreover the pharmaceutical composition exhibits tolerogenic effect for the correction of pathological conditions, associated with increased production of proinflammatory cytokines (Example 4C).

The pharmaceutical composition was developed comprising the effective amount of the combination of the modified lipopolysaccharides (S-LPS) of endotoxic bacteria—di-acylated and tri-acylated derivatives or di-acylated and tetra-acylated derivatives, or tri-acylated and tetra-acylated derivatives, or di-acylated, tri-acylated and tetra-acylated derivatives. The claimed pharmaceutical composition is the immune system response modulator in mammals, including humans (Example 4B, 4C); combinations of the modified lipopolysaccharides containing in its formulation are apyrogenic for a rabbit in a dose of up to 100 mcg/kg in the rabbit pyrogenicity test (Example 2C).

The claimed pharmaceutical composition may comprise pharmaceutically acceptable targeted additives, which may be preservatives or stabilizers, or solvents, or combinations thereof.

The claimed pharmaceutical composition has broad-spectrum pharmacological activity and notably exhibits effective therapeutic antiviral action against infection caused by influenza A H1N1 virus (Example 4B). Moreover the pharmaceutical composition exhibits tolerogenic effect for the correction of pathological conditions, associated with increased production of proinflammatory cytokines (Example 4C).

It should also be noted that undoubted advantage of the claimed medicaments (vaccine and pharmacompositions) in comparison with medicaments-analogues of other classes is their excellent chemical and pharmaceutical characteristics: thermostability, well known for LPS molecules, providing the possibility to its extended storage period, relative environmental resistance.

A use of the modified lipopolysaccharide (S-LPS) of endotoxic bacteria—its di-acylated or tri-acylated, or tetra-acylated derivative is also claimed in the manufacture of a medicament.

Meanwhile the modified lipopolysaccharide generates protection against *Salmonella, Escherichia, Shigella, Bordetella, Haemophilus, Neisseria, Campylobacter, Vibrio, Klebsiella, Chlamydia, Corynebacterium* and combinations thereof by inducing a synthesis of specific antibacterial IgG, IgA, IgM antibodies in mammals, including humans (Examples 2D, 3C), provides prophylaxis and/or correction of the course of septic and endotoxic shock (Example 3D), is the immune system response modulator in mammals, including humans (Example 4C); and is apyrogenic for a rabbit in a dose of up to 100 mcg/kg in the rabbit pyrogenicity test (Example 2B).

The medicament is intended for parenteral, peroral, rectal, intra-vaginal, transdermal, sublingual and aerosol administration to mammals, including humans.

The use of the combinations of the modified lipopolysaccharides (S-LPS) of endotoxic bacteria—di-acylated and tri-acylated derivatives or di-acylated and tetra-acylated derivatives, or tri-acylated and tetra-acylated derivatives, or di-acylated, tri-acylated and tetra-acylated derivatives is claimed in the manufacture of a medicament.

Meanwhile the combinations of the modified polysaccharides generate protection against *Salmonella, Escherichia, Shigella, Bordetella, Haemophilus, Neisseria, Campylobacter, Vibrio, Klebsiella, Chlamydia, Corynebacterium* and combinations of them by inducing a synthesis of specific antibacterial IgG, IgA, IgM antibodies in mammals, including humans (Examples 2D, 3F), provide anti-shock activity for septic and endotoxic shock (Example 3D), are the immune system response modulators in mammals, including humans (Examples 3F, 4B, 4C); and are apyrogenic for a rabbit in a dose of up to 100 mcg/kg in the rabbit pyrogenicity test (Example 2C).

The medicament is intended for parenteral, peroral, rectal, intra-vaginal, transdermal, sublingual and aerosol administration to mammals, including humans.

The use of the modified lipopolysaccharide (S-LPS)—its di-acylated or tri-acylated, or tetra-acylated derivative is claimed as an immunostimulating carrier in the manufacture of a vaccine against bacterial, viral and other infections.

Meanwhile the modified lipopolysaccharide is conjugated with protective antigen or hapten, which preferably has synthetic or protein, or polysaccharide nature.

The modified polysaccharide is apyrogenic for a rabbit in a dose of up to 100 mcg/kg in the rabbit pyrogenicity test (Example 2C).

The use of the combinations of modified lipopolysaccharides (S-LPS)—di-acylated and tri-acylated derivatives or di-acylated and tetra-acylated derivatives, or tri-acylated and tetra-acylated derivatives, or di-acylated, tri-acylated and tetra-acylated derivatives is claimed as an immunostimulating carrier in the manufacture of a vaccine against bacterial, viral and other infections.

Meanwhile the modified lipopolysaccharides are conjugated with protective antigen or hapten, which preferably have synthetic or protein, or polysaccharide nature.

The combinations of the modified lipopolysaccharides are apyrogenic for a rabbit in a dose of up to 100 mcg/kg in the rabbit pyrogenicity test (Example 2C).

BRIEF DESCRIPTION OF THE DRAWINGS

The inventions are illustrated by the following figures.

The solid lines represent the lines of extrapolation for the values of doses for OM174: 0.20; 2.00; 2.01; 3.40 and 28.10 (A and B) and the values of doses for Westphal LPS *E coli* O:111B4: 0.002; 0.020; 0.200 and 2.000 (C).

Figure 2:
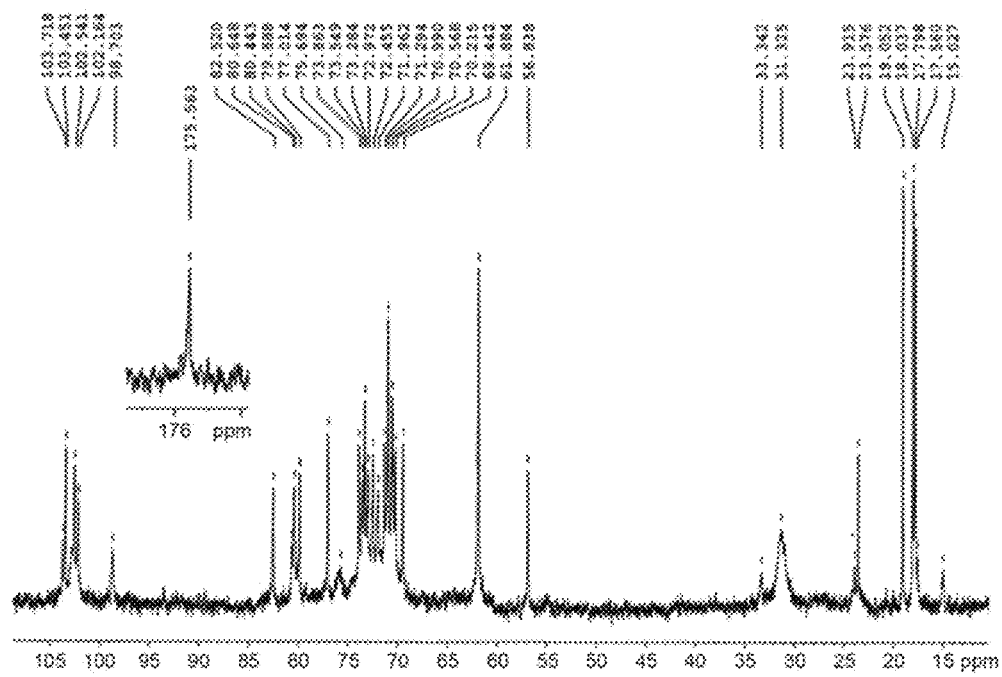

FIG. 2 shows $^{13}$C-NMR-spectrum of *S. flexneri* 2a deacylated S-LPS.

Figure 3:
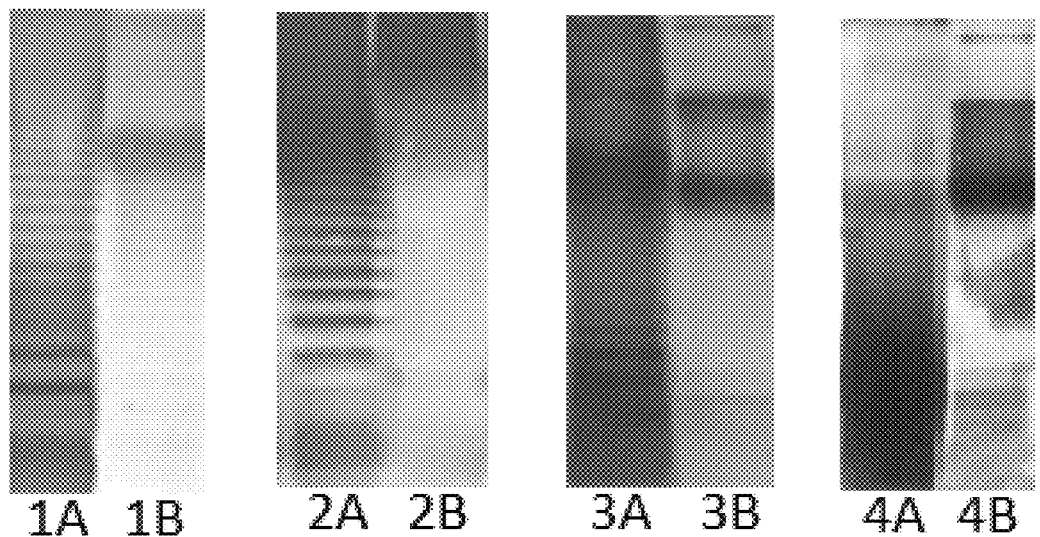

FIG. 3 shows the photographs of silver staining tracks obtained after SDS-PAGE for the samples of the original LPS Westphal (A) and the modified S-LPS (B) *S. flexneri* 2a (1A, 1B), *E. coli* O:55 (2A, 2B), *K. pneumoniae* (3A, 3B), *S. enterica* sv *typhi* O:901 (4A, 4B).

Figure 4:
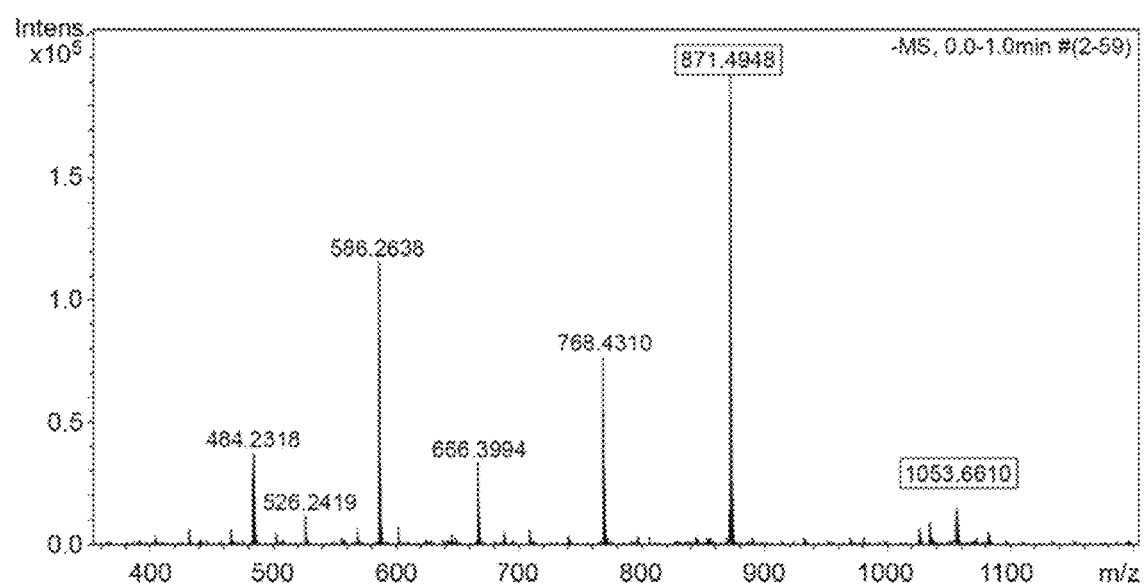

FIG. 4 shows ESI-MS mass-spectrum of lipid A obtained from *S. flexneri* 2a diacylated S-LPS.

Figure 5:
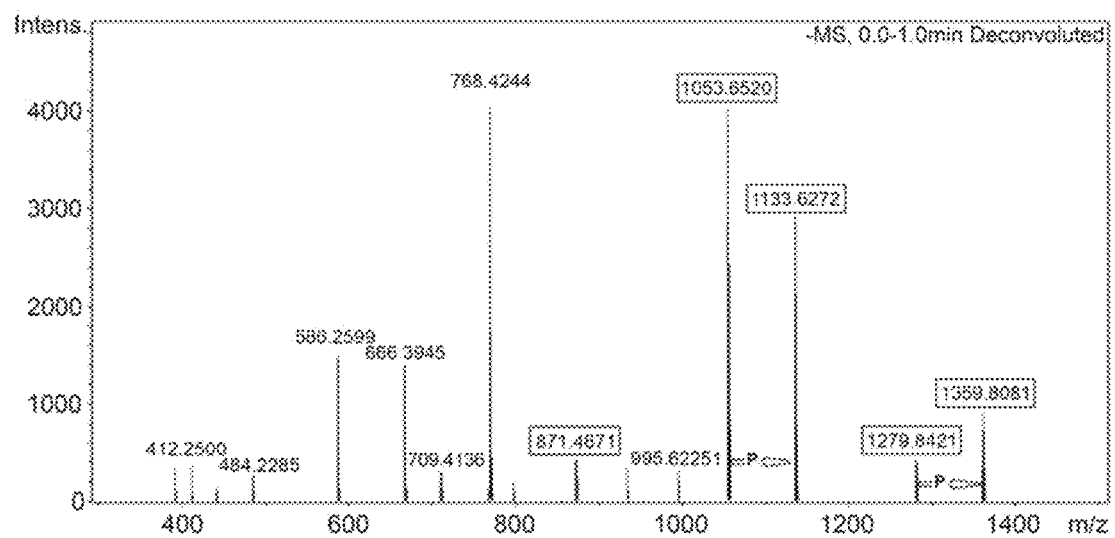

FIG. 5 shows ESI-MS mass-spectrum of lipid A obtained from *S. flexneri* 2a triacylated S-LPS.

Figure 6:
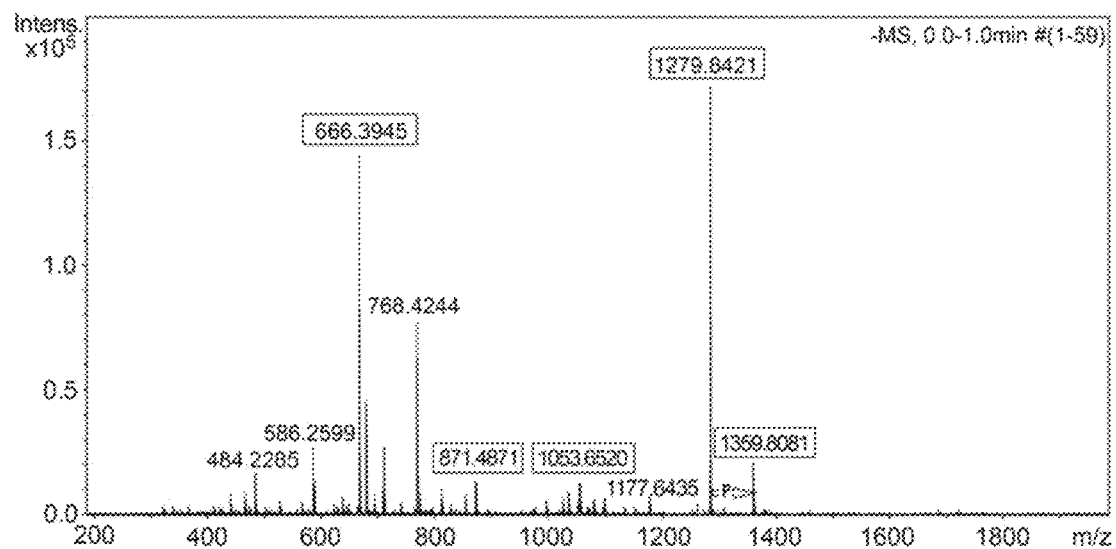

FIG. 6 shows ESI-MS mass-spectrum of lipid A obtained from *S. flexneri* 2a tetraacylated S-LPS.

Figure 7:
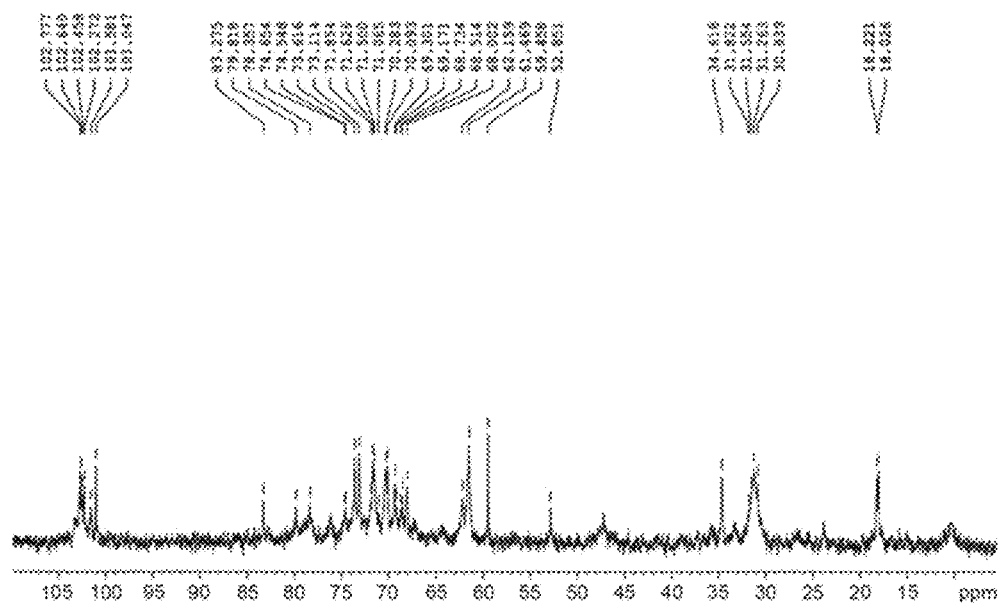

FIG. 7 shows $^{13}$C-NMR-spectrum of pre-deacylated *S. enterica* sv *typhi* O: 901 S-LPS.

Figure 8A:
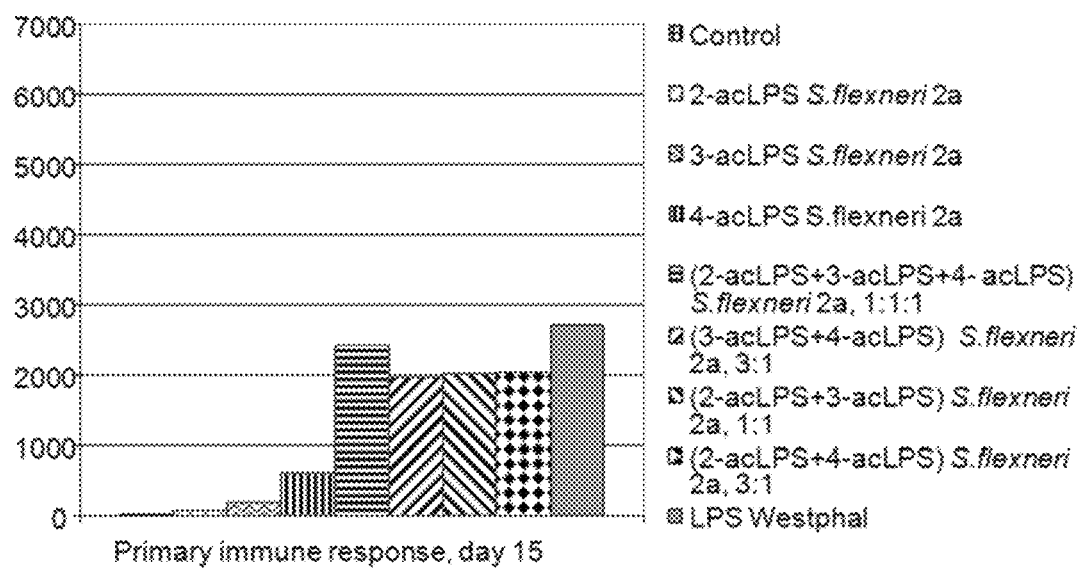
Figure 8B:
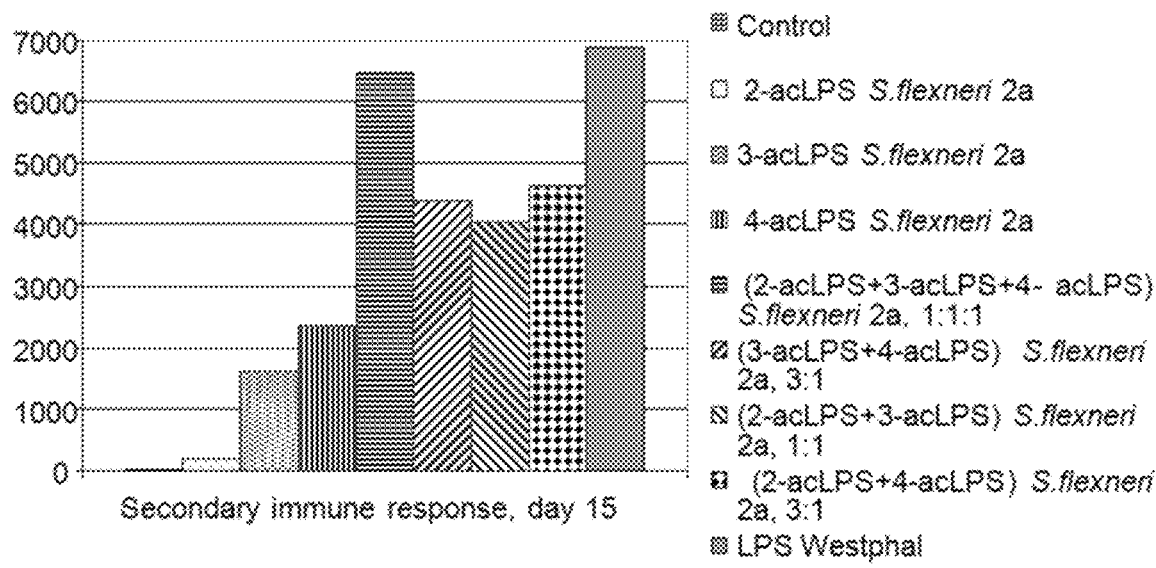

FIG. 8 shows the diagrams of IgG antibody production (day 15) after primary (A) and secondary (B) immunization of mice with preparations made with 2-acLPS, 3-acLPS 4-acLPS *S. flexneri* 2a, and also combinations thereof (2-acLPS+3-acLPS+4-acLPS), (3-acLPS+4-acLPS), (2-acLPS+3-acLPS) and (2-acLPS+4-acLPS) with component mass ratio 1:1:1, 3:1, 1:1 and 3:1, respectively, and the preparation made with Westphal LPS *S. flexneri* 2a, at a dose of 25 mcg per mouse. The vertical axis represents the value of titer serum dilution.

Figure 9A:
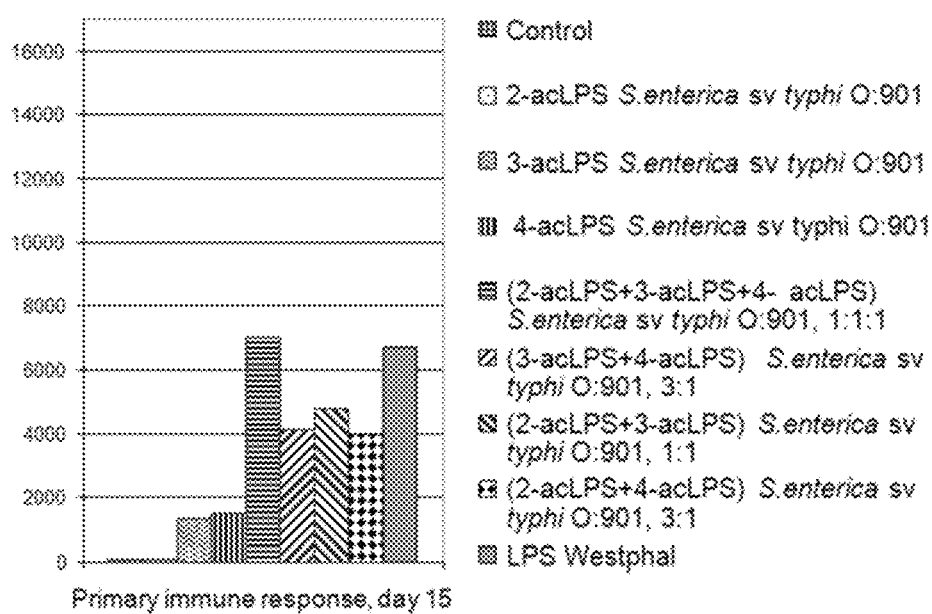
Figure 9B:
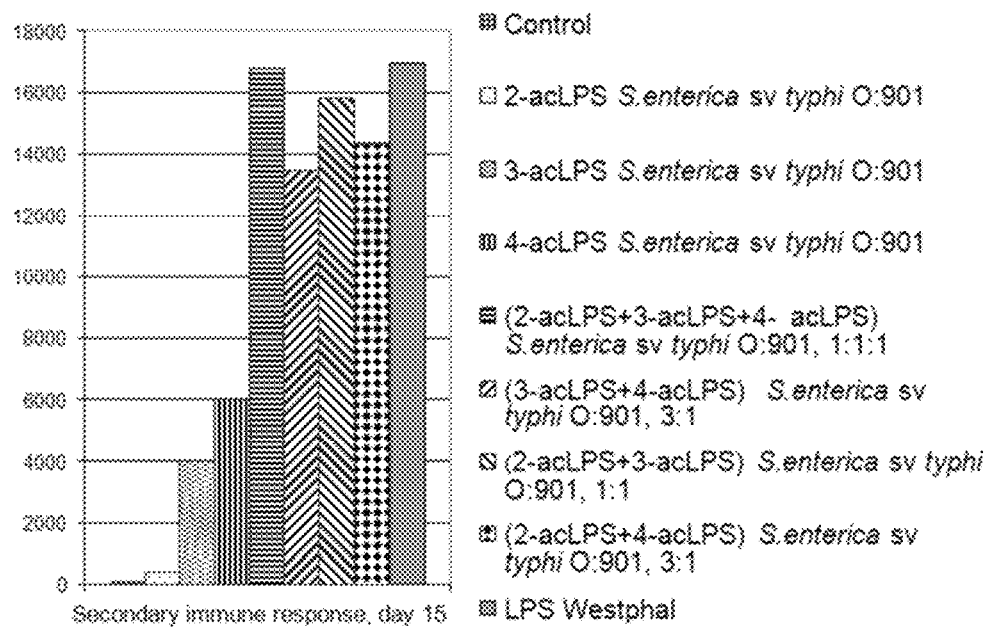

FIG. 9 shows the diagrams of IgG antibody production (day 15) after primary (A) and secondary (B) immunization of mice with preparations made with 2-acLPS, 3-acLPS 4-acLPS *S. enterica* sv *typhi* O:901, and also combinations thereof (2-acLPS+3-acLPS+4-acLPS), (3-acLPS+4-acLPS), (2-acLPS+3-acLPS) and (2-acLPS+4-acLPS) with component mass ratio 1:1:1, 3:1, 1:1 and 3:1, respectively, and the preparation made with Westphal LPS *S. enterica* sv *typhi* O:901, at a dose of 25 mcg per mouse. The vertical axis represents the value of titer serum dilution.

Figure 10A:
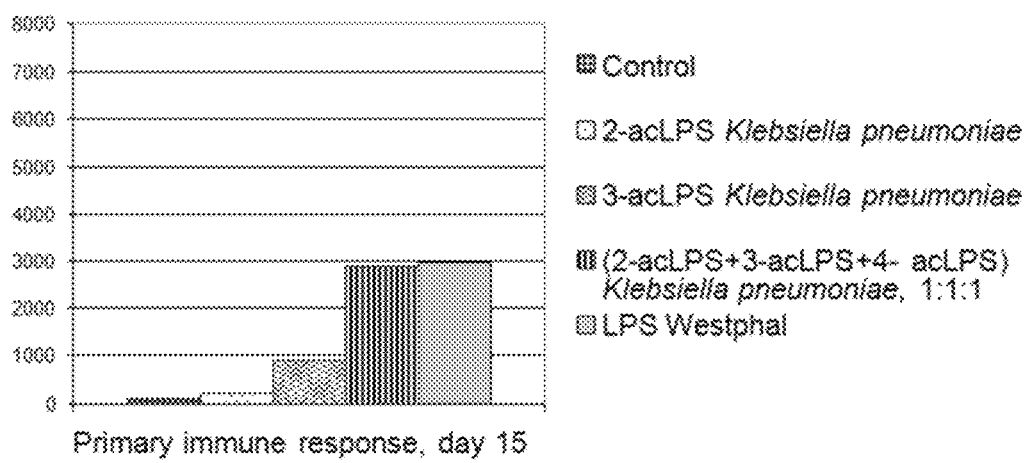
Figure 10B:
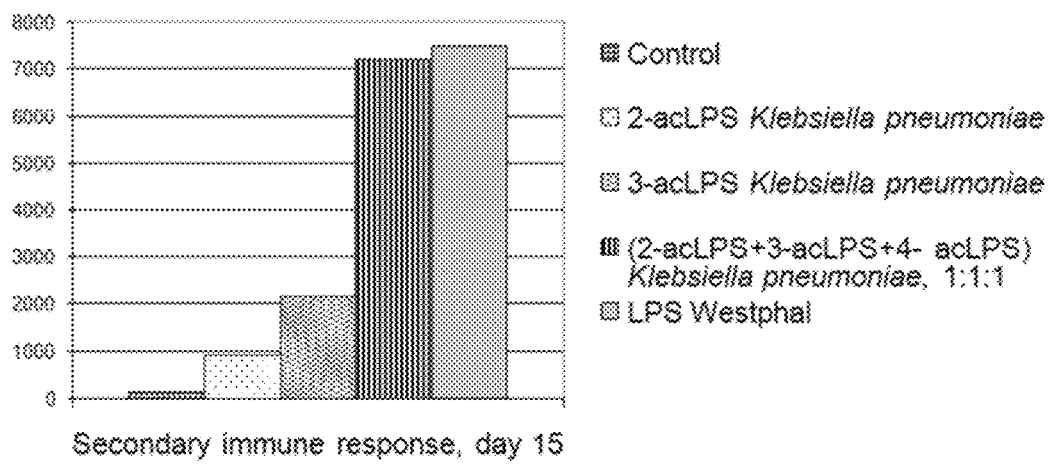

FIG. 10 shows the diagrams of IgG antibody production (day 15) after primary (A) and secondary (B) immunization of mice with preparations made with 2-acLPS and 3-acLPS *K. pneumoniae*, and also combinations thereof (2-acLPS+3-acLPS+4-acLPS) with component mass ratio 1:1:1, and preparation made with Westphal LPS *K. pneumoniae*, at a dose of 25 mcg per mouse. The vertical axis represents the value of titer serum dilution.

Figure 11A:
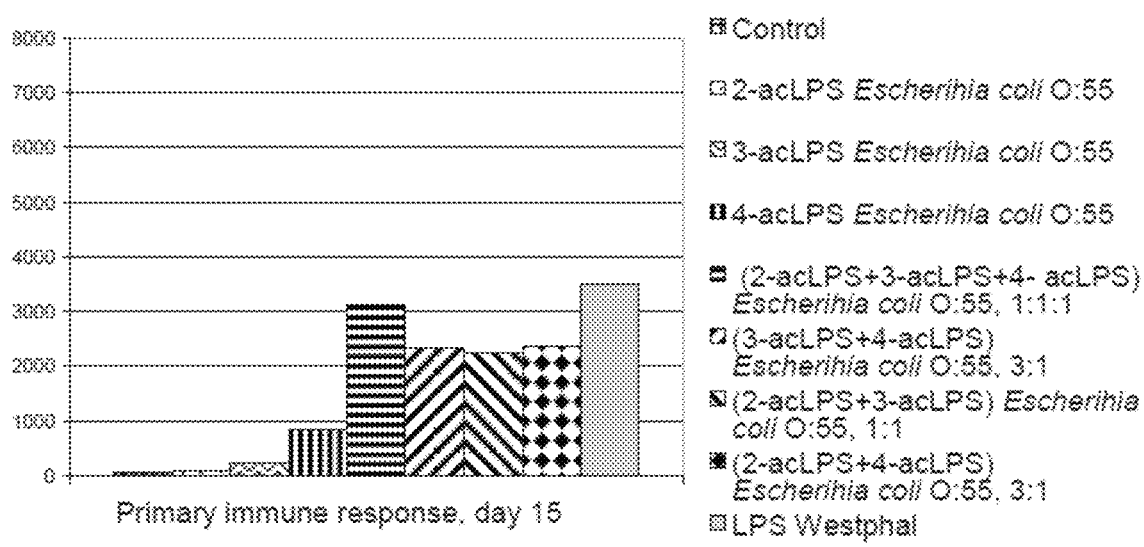
Figure 11B:
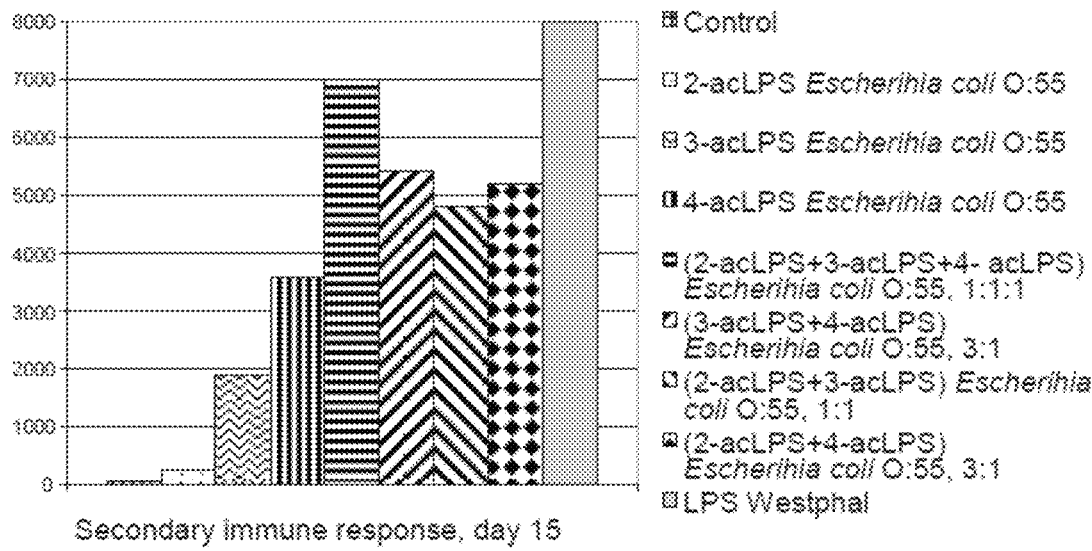

FIG. 11 shows the diagrams of IgG antibody production (day 15) after primary (A) and secondary (B) immunization of mice with preparations made with 2-acLPS, 3-acLPS and 4-acLPS *E. coli* O:55, and also combinations thereof (2-acLPS+3-acLPS+4-acLPS), (3-acLPS+4-acLPS), (2-acLPS+3-acLPS) and (2-acLPS+4-acLPS) with component mass ratio 1:1:1, 3:1, 1:1 3:1, respectively, and the preparation made with Westphal LPS *E. coli* O:55, at a dose of 25 mcg per mouse. The vertical axis represents the value of titer serum dilution.

Figure 12A:
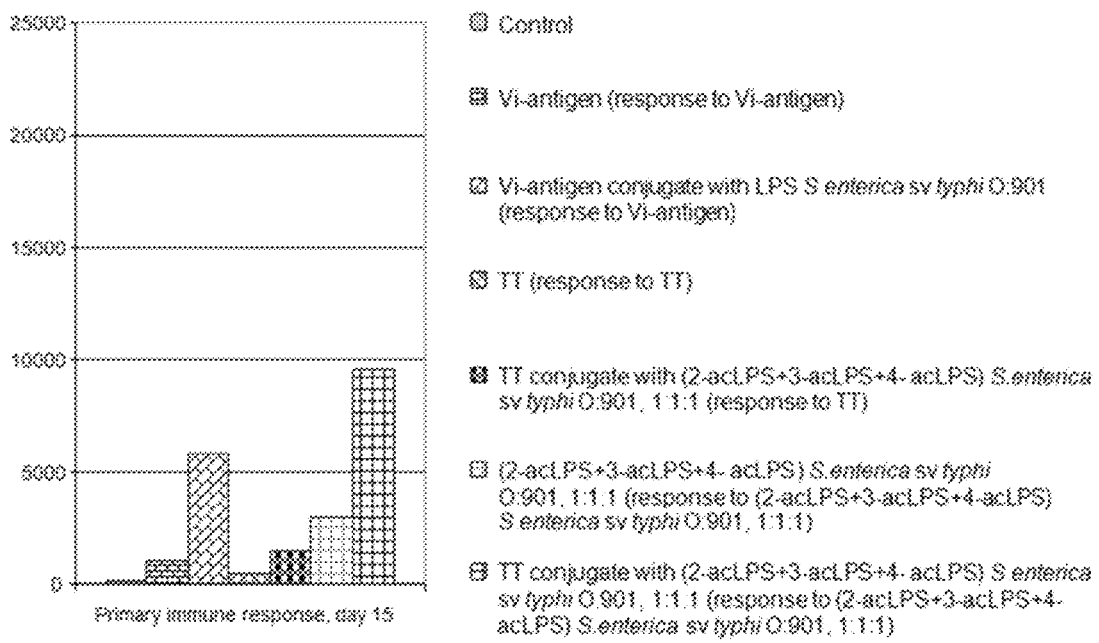
Figure 12B:
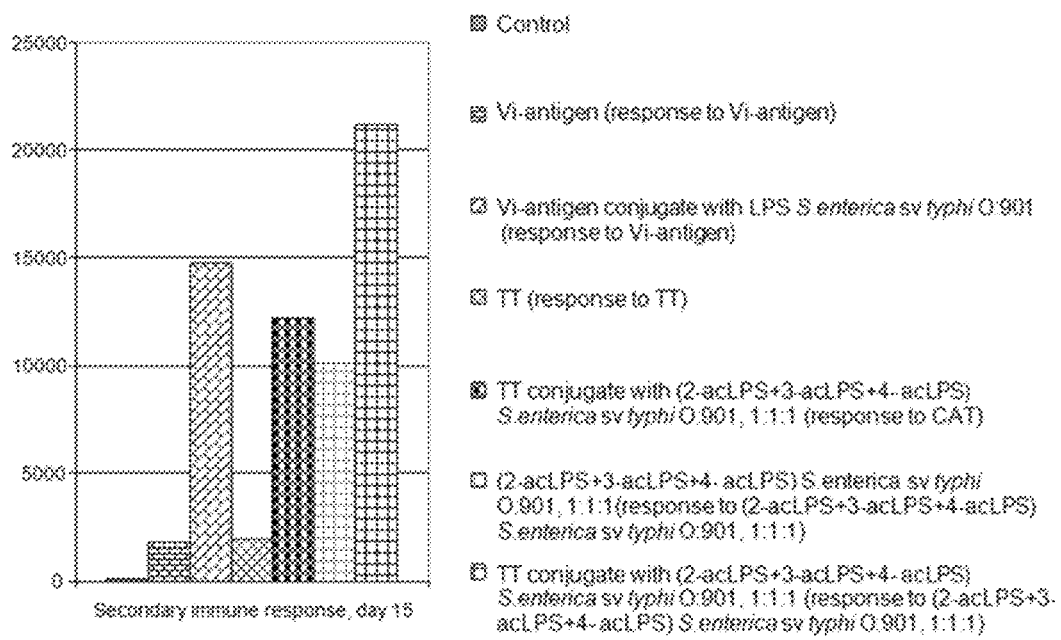

FIG. 12 shows the diagrams of IgG antibody production (day 15) after primary (A) and secondary (B) immunization of mice with conjugations made with Vi-antigen and Tetanus Toxoid (TT) with immunostimulating carrier—the combination of (2-acLPS+3-acLPS+4-acLPS) *S. enterica* sv *typhi* O:901 with component mass ratio 1:1:1, and also pure Vi-antigen and TT, at a dose of 25 mcg of polysaccharide or 20 mcg of protein per mouse. The vertical axis represents the value of titer serum dilution.

Figure 13A:
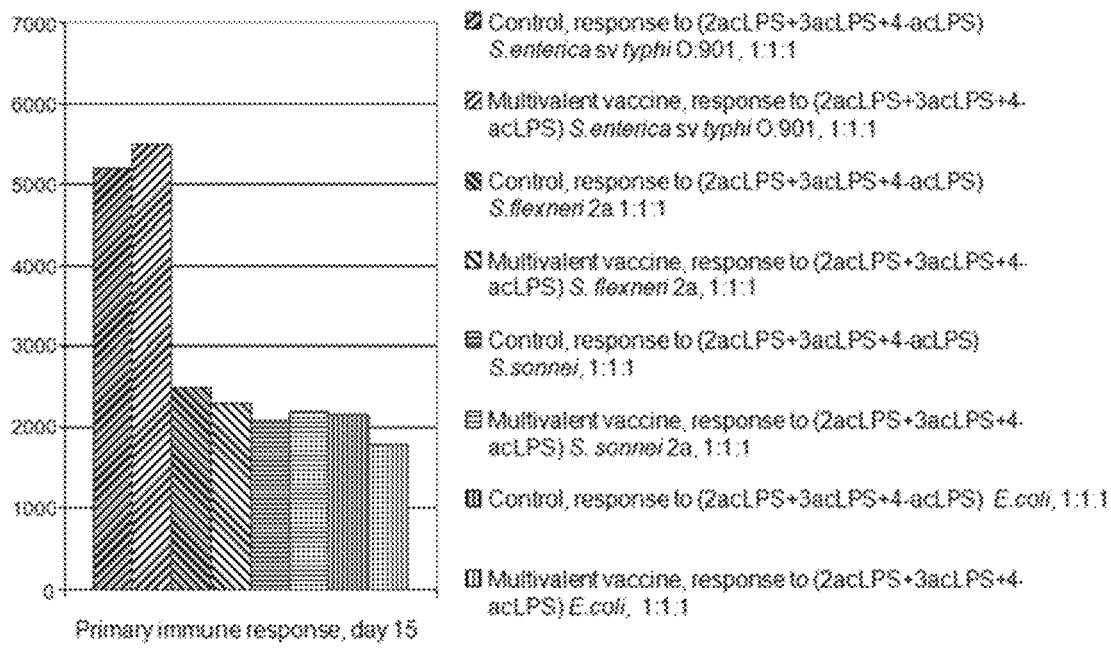
Figure 13B:
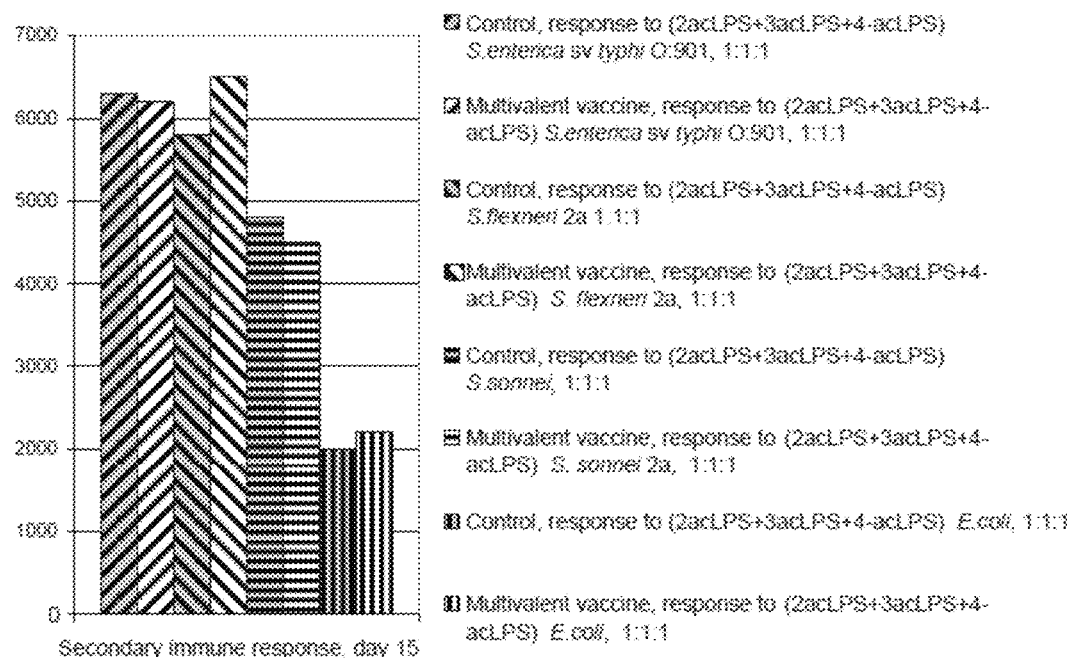

FIG. 13 shows the diagrams of IgG antibody production (day 15) after primary (A) and secondary (B) immunization of mice with multivalent dysentery-typhoid-*escherichia* vaccine at a dose of 100 mcg per mouse, and also individual components thereof—combination of (2-acLPS+3-acLPS+4-acLPS) in mass ratio 1:1:1, *S. flexneri* 2a or *S. sonnei*, or *S. enterica* sv *typhi* O:901, or *E. coli* O:55, at a dose of 25 mcg per mouse. The vertical axis represents the value of titer serum dilution.

Figure 14:
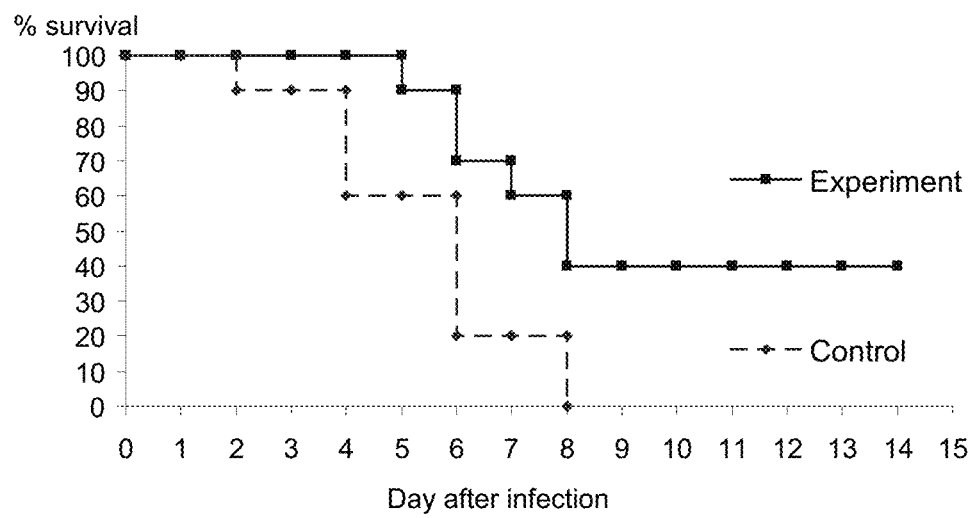

FIG. 14 shows graphs of survival rates of two groups of mice, infected with a dose of LD100 of virulent influenza strain A subtype H1N1.

PREFERRED EMBODIMENTS

Example 1

In Vivo Induction of TNF-α the Mediator of Endotoxin Reaction after Intravenous (i.v.) Administration of the Modified S-LPS and the Modified Lipids A of Endotoxic Bacteria to Mice According to data from patent RU 2154068, tri-acylated and tetra-acylated lipids A of *E. coli, H. influenzae* and *P. aeruginosa* are powerful inducers of mediator of endotoxin reaction—TNF-α. Table 1 represents data extrapolated from graphs on FIG. 1 (A, B, C) relating to in vivo TNF-α production in serum after i.v. administration of tri-acylated lipid A (3-acLA) of *E. coli* OM-174 and Westphal LPS *E. coli* O:111B4 to mice. Only 10-fold difference was detected for induction of TNF-α in vivo between *E. coli* OM-174 tri-acylated lipid A and commercially available endotoxin Westphal LPS *E. coli* O:111 B4, it is evidence that there is essential endotoxicity of *E. coli* tri-acetylated lipid A, excluding its use both as vaccine or vaccine component (adjuvant).

and lipids of mentioned bacteria were obtained as per Example 2A. The amount of TNF-α was determined in mouse sera using test system Quantikine Mouse TNF-α/TNFSF1A (R&D Systems, USA) by ELISA according to manufacturer's standard protocol. Animal sera blood samples were taken 90 minutes after administration.

The Data presented in Table 2 prove that in contrast to the modified lipids A, corresponding modified S-LPS of enterobacteria are poor inducers of TNF-α the mediator of endotoxic shock and can be used as vaccine preparations.

TABLE 2

TNF-α concentration (pg/mL) in serum after 2 hours after i.v. administration of the modified S-LPS and modified lipids A from enterobacteria to mice.

| Preparation/dose administration | *S.flexneri* 2a | | *Senterica* sv *typhi* O:901 | | *E.coli* O:55 | | *K.pneumoniae* | |
|---|---|---|---|---|---|---|---|---|
| | S-LPS | Lipid A | S-LPS | Lipid A | S-LPS | LipidA | S-LPS | LipidA |
| | 2-acLPS | 2-acLA | 2-acLPS | 2-acLA | 2-acLPS | 2-acLA | 2-acLPS | 2-acLA |
| 50 mg/kg | 15 | 126 | 24 | 159 | 19 | 142 | 22 | 134 |
| 5 mg/kg | 13 | 75 | 19 | 101 | 18 | 57 | 11 | 53 |
| 2.5 mg/kg | 14 | 29 | 11 | 38 | 15 | 47 | 13 | 37 |
| | 3-acLPS | 3-acLA | 3-acLPS | 3-acLA | 3-acLPS | 3-acLA | 3-acLPS | 3-acLA |
| 50 mg/kg | 57 | 315 | 82 | 427 | 53 | 404 | 42 | 233 |
| 5 mg/kg | 26 | 103 | 39 | 162 | 22 | 171 | 22 | 113 |
| 2.5 mg/kg | 14 | 54 | 21 | 103 | 14 | 58 | 22 | 47 |
| | 4-acLPS | 4-acLA | 4-acLPS | 4-acLA | 4-acLPS | 4-acLA | 4-acLPS | 4-acLA |
| 50 mg/kg | 170 | 1218 | 202 | 1113 | 132 | 982 | 101 | 457 |
| 5 mg/kg | 124 | 315 | 150 | 402 | 84 | 323 | 62 | 117 |
| 2.5 mg/kg | 42 | 103 | 63 | 134 | 32 | 51 | 24 | 82 |

TABLE 1

In vivo production of TNF-α the mediator of endotoxin reaction in blood serum after i.v. administration of *E coli* OM-174 tri-acylated lipid A and Westphal LPS *E. coli* O:111B4 to mice by data from patent RU 2154068

| Preparation | Dose administration to mice (mg/kg) | TNF-α concentration (pg/mL) |
|---|---|---|
| 3-acLA *E. coli* - OM174 | 0.2 | 328 |
| | 2.0 | 1644 |
| | 2.01 | 1416 |
| | 3.4 | 2000 |
| | 28.1 | 2750 |
| Westphal LPS *E. coli* O:111B4 | 0.002 | 400 |
| | 0.020 | 1333 |
| | 0.2 | 2800 |
| | 2.0 | 4733 |
| Saline solution (0.9%-NaCl solution) | 0 | 0 |

The comparative study of in vivo induction of TNFα the mediator of endotoxin reaction after i.v. administration of di-acylated S-LPS (2-acLPS), tri-acylated S-LPS (3-acLPS), tetra-acylated S-LPS (4-acLPS) and corresponding di-acylated lipids A (2-acLA), tri-acylated lipids A (3-acLA), tetra-acylated lipids A (4-acLA), obtained from actual enterobacteria *S. flexneri* 2a, *S. enterica* sv *typhi* O:901, *E. coli* O:55, *K. pneumoniae*, has revealed significant differences in cytokine concentration in animal sera. Obtained data are provided in Table 2, in this case the modified S-LPS Example 2

Preparation and Characteristics of Individual Modified S-LPS of Endotoxic Bacteria and Combinations Thereof.

A. Preparation of individual modified S-LPS of endotoxic bacteria and combinations thereof Bacterial culture of *S. flexneri* 2a was prepared in liquid medium by deep cultivation. Separation of bacterial cells from liquid phase was performed by flow centrifuge. Obtained wet cells were washed first with saline solution then with water and then they were lyophilized.

20 g of dried bacterial cell were extracted by the Westphal method (Westphal O., Luderitz O. Chemische Erforschung von Lipopolysacchariden Gram-negativer Bakterien. Angew. Chemie., 1954, vol. 66, pp. 407-17) with hot 45%-aqueous phenol at 68-70° C.; 960 mg of crude LPS was obtained from aqueous phase followed by successive dialysis and lyophilisation and it then was re-dissolved in 0.05 M TRIS-buffer solution, pH=7.2, containing 0.01% (w/w) $CaCl_2$) and $MgCl_2$, RNAse and DNAse was added in concentration 100 mcg/mL and 10 mcg/mL, respectively, and after 16 hours of stirring at 37° C. the reaction mixture was treated with proteinase K (20 mcg/mL) for 2 hours at 55° C. The resulting solution was dialyzed using the Vladisart installation for ultrafiltration with the limit of the passage of the membrane 50 kDa.

The dialyzed solution was concentrated and then lyophilized to give 530 mg of isolated LPS, containing not more than 2% (w/w) of protein, determined by the Bradford method (Bradford M. M. A rapid and sensitive method for the quantitation of microgram quantities of protein utilizing the principle of protein-dye binding. Anal. Biochem., 1976, vol. 72, pp. 248-54), and not more than 2% (w/w) of nucleic acid, determined by the Spirin method (Spirin A. S. Spectrophotometric determination of the total amount of nucleic acids. Biochemistry, 1958, v. 23, No. 4, p. 656).

Figure 1A:
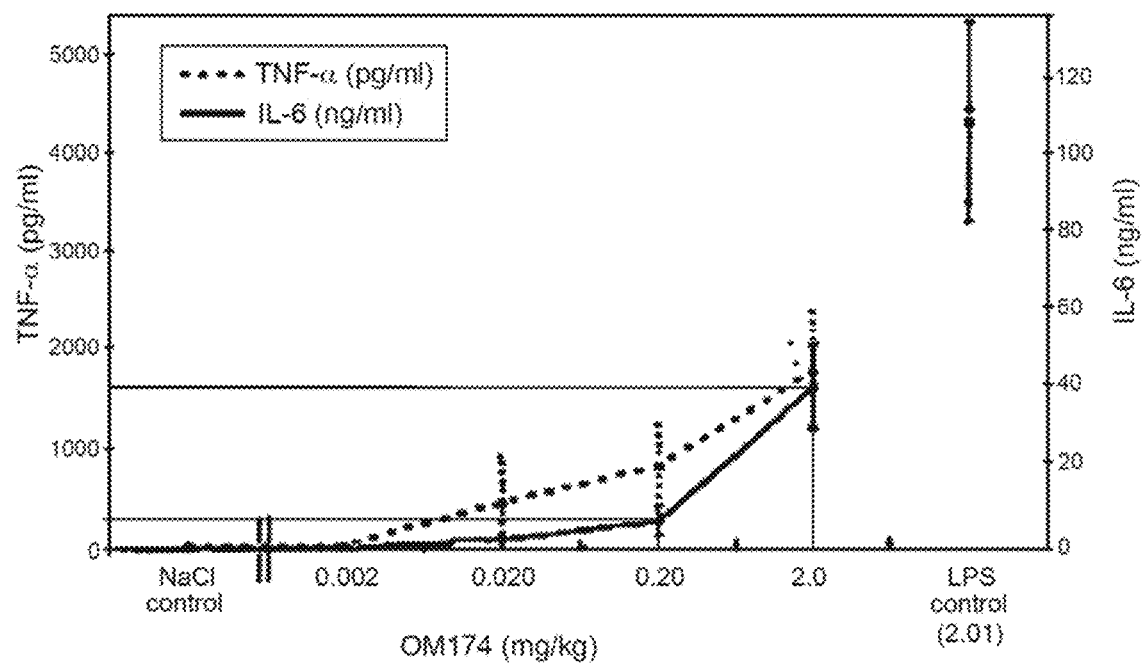
FIG. 1 shows graphs of in vivo production of TNF-α the mediator of endotoxin reaction and proinflammatory cytokine IL-6 in blood sera after intravenous administration to mice of tri-acylated lipid A *E. coli* OM174 (A and B) and Westphal LPS *E coli* O:111B4 (C) based on data from patent RU 2154068. In this case the vertical axis represents the values for TNF-α concentrations (pg/mL) and the values for IL-6 concentrations (ng/mL). The horizontal axis represents (A and B) the values for injection dose of preparation OM174 (mg/kg) to mice. The vertical axis (C) represents the value for injection dose of LPS (mg/mL; positive control) and saline solution (0.85% NaCl solution; negative control) to mice.
Figure 1B:
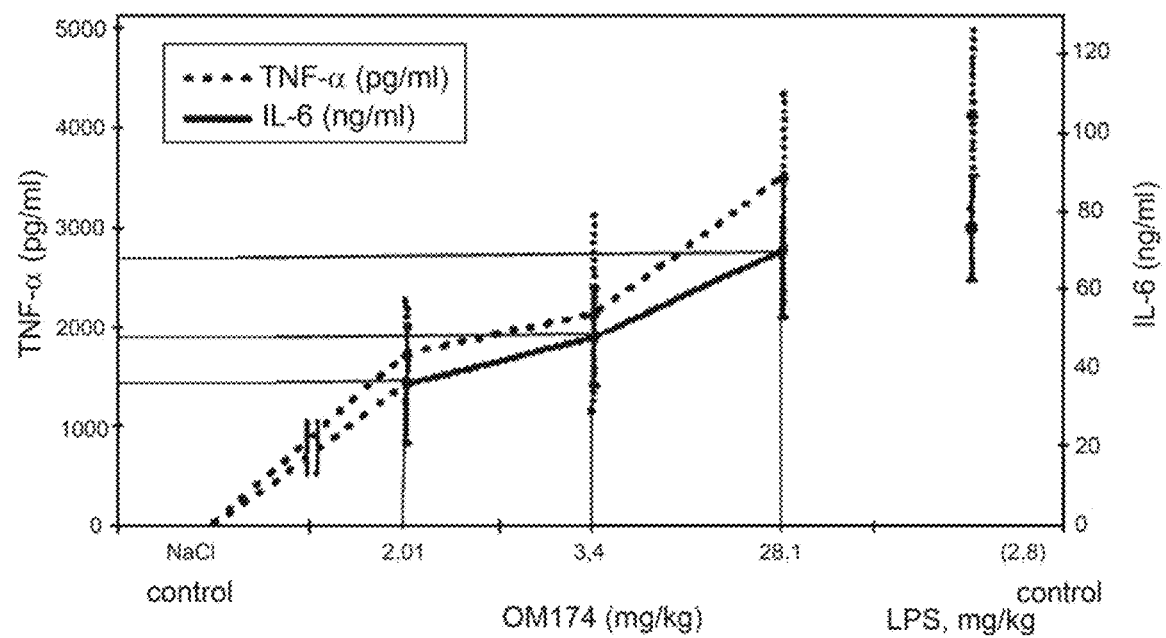
Figure 1C:
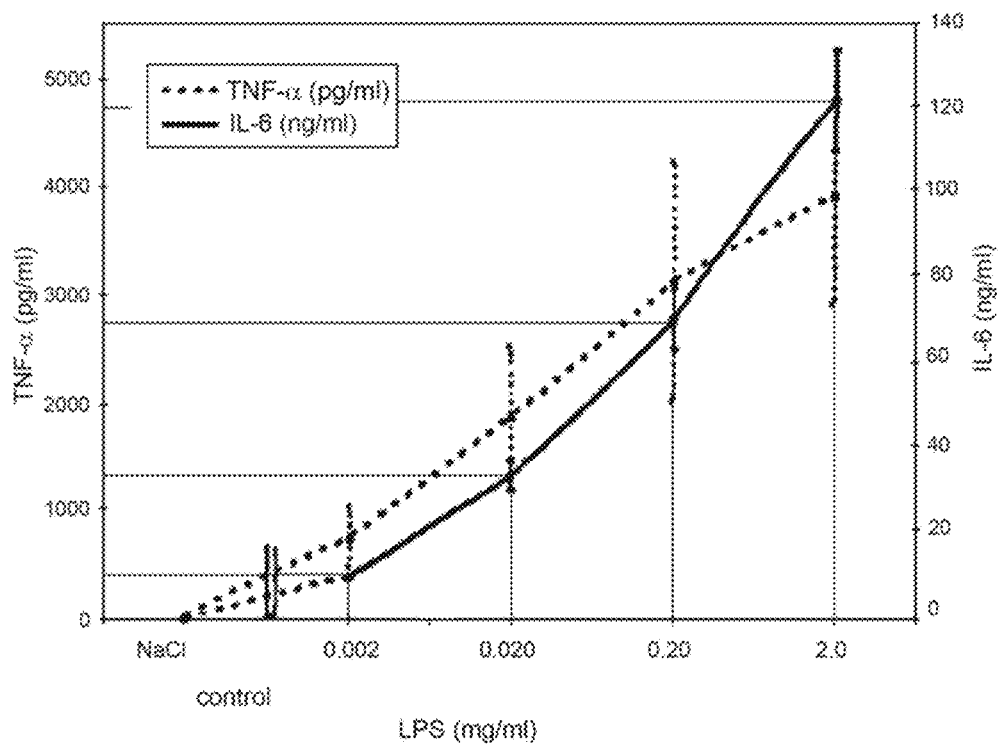

Prepared LPS was characterized by SDS-PAGE data, which demonstrated the «classic» picture of a set of correctly alternating bands, each of them corresponded to S-LPS molecule with definite number of repeating units in O-specific polysaccharide chain, moreover the fastest migrating (the lowermost) zone corresponded to R-LPS (FIG. 3 1A).

LPS isolated from dried bacterial cells S. flexneri 2a was dissolved in aqueous ammonia, the obtained solution was stirred on magnetic plate and then cooled to 5-10° C. Reaction mixture was neutralized by 10% hydrochloric acid; the obtained solution was poured into 8-10-fold volume of ethanol with stirring, precipitation was separated by centrifugation and then the precipitation procedure was repeated twice, the obtained precipitate was dissolved in alcohol and then the obtained solution was lyophilizied. Hence pure partially deacetylated S-LPS was obtained, that was proved by electrophoresis data (FIG. 3; 1A). Partially deacylated S-LPS composed of di- or tri-, or tetra fatty acid residues (di-, tri- and tetra-acylated derivatives—2-acLPS, 3-acLPS and 4-acLPS) in lipid component was prepared by varying the condition of alkaline degradation of S.flexneri 2a LPS, in particular, the temperature and time of saponification reaction and also concentration of ammonia hydroxide.

B. Structure, composition and physico-chemical properties of individual modified S-LPS Data about fatty acid composition were obtained based on the analysis of lipid A of each S-LPS extracted from each S-LPS by mild hydrolysis (1% AcOH, 100 degree, 1 hour).

FIG. 4, FIG. 5 and FIG. 6 represent typical mass-spectra of lipids A, prepared from deacylated S-LPS S. flexneri 2a. The characteristic signals in mass-spectra are m/z 871, 1053 and 1279 (excluding contributions of m/z). These major signals in each spectrum correspond to di- (FIG. 4), tri- (FIG. 5) and tetra-acylated (FIG. 6) derivatives of lipid A, respectively. It is necessary to notice a total absence of signals of penta- and hexa-acylated (m/z 1506 and 1716 respectively) derivatives in mass-spectra of deacylated lipids A, which intensity was very high in the spectra of lipid A from initial S-LPS.

For the evaluation of ratio between major and minor/minor components in the obtained products of deacylated S-LPS, the intensity of corresponding signals in mass-spectra was measured. The peaks intensity corresponding not only to mono- and diphosphorilated derivatives was taken into consideration. In the case of di-acylated S-LPS the content of the main substance was 91% (w/w), in the case of tri-acelated one—85% (w/w), and in the case of tetra-acylated one—88% (w/w). High resolution mass-spectrometry with electrospray ionization and ion detection using ion-cyclotron resonance was performed on a Bruker Daltonics spectrometer, model Apex II, with magnet 7 (Tesla).

Also, analysis of LPS and obtained partially deacylated S-LPS was carried out by $^{13}$C-NMR spectra. $^{13}$C-NMR-spectroscopy was performed by Bruker spectrometer, model DRX-500, with XWINNMR software and impulse sequences from the manufacturer. Registration of spectra was conducted in $D_2O$ (99:95%) with acetone as a standard (31.5 ppm). Comparison of $^{13}$C-NMR-spectra of initial and partially deacylated S-LPS showed its full identity, except broad signal, corresponding to methylene residues of fatty acid from lipid A at the region 30-34 ppm, the integral intensity of which significantly reduced in spectra of S-LPS obtained after alkaline degradation. Additionally comparative analysis of $^{13}$C NMR-spectra demonstrates that there are no changes of primary structure of O-PS repeating units during modification (deacylation) of LPS.

FIG. 2 shows the representative $^{13}$C-NMR-spectrum of di-acylated S-LPS S. flexneri 2a, in which spectrum of region belonging to polysaccharide component is fully identical to spectrum of O-PS isolated from corresponding unmodified S-LPS. Complete coincidence of obtained spectra data with literature data (Andrei V. Perepelov, Vyacheslav L. L'vov, Bin Liu, Sofya N. Senchenkova, Maria E. Shekht, Alexander S. Shashkov, Lu Feng, Petr G. Aparin, Lei Wang, Yuriy A. Knirel. A similarity in the O-acetylation pattern of the O-antigens of Shigella flexneri types 1a, 1b, 2a. Carbohydr. Res., 2009, vol. 344, pp. 687-92) indicates that prepared product is deacylated S-LPS with long O-PS chains, because there are no signals belong to oligosaccharide core in the spectrum.

The content of proteins and nucleic acids in obtained preparations did not exceed 1% (w/w).

Native S-LPS is extracted from dried bacterial cells S. enterica sv typhi or E. coli O:55 by abovementioned method (Example 2A) and then it was subjected to alkaline treatment to obtain pre-deacylated S-LPS, from which its individual di-, tri-, tetra-acylated were further isolated. $^{13}$C-NMR-spectrum of pre-deacylated S-LPS S. enterica sv typhi is reperesented on FIG. 7. Individual di-, tri- and tetra-acylated S-LPS from K. pneumoniae bacterium were extracted from commercially available sample of S-PLS of K. pneumoniae bacteria (Sigma L4288) by the same approach. Electrophoresis data (FIG. 3, 2A-4B) shows that products are S-LPS, isolated from S. enterica sv typhi O:901, K. pneumoniae, E. coli O:55.

Lyophilized substances were obtained before for the study of immunobiological properties of combinations of deacylated S-LPS of endotoxic bacteria. Substance of two-component combination was prepared by dissolution of 2-acLPS and 3-acLPS; 2-acLPS and 4-acLPS; 3-acLPS and 4-acLPS at required mass ratio in apyrogenic water, and then obtained solution was lyophilized. The substance of three-component combination was prepared containing 2-acLPS, 3-acLPS and 4-acLPS at mass ratio 1:1:1 in similar fashion.

C. Pyrogenicity of individual modified S-LPS and combinations thereof. Low and clinically applicable endotoxicity level of preparation of individual deacylated S-LPS of endotoxic bacteria and combinations thereof was proved by special pyrogenicity studies in the experimental animals in vivo and by clinical studies of pyrogenicity and safety. Pyrogenicity of preparations of individual modified S-LPS—2-acLPS, 3-acLPS, 4-acLPS and combinations thereof—(2-acLPS+3-acLPS+4-acLPS), (3-acLPS+4-acLPS), (2-acLPS+3-acLPS), (2-acLPS+4-acLPS) of S. flexneri 2a, S. enterica sv typhi O:901, K. pneumoniae, E. coli O:55 bacteria, and also LPS, obtained from S. flexneri 2a by the classic Westphal method was determined in comparison with commercial Vi-antigen vaccine. The test was conducted on Chinchilla rabbits weighing 2.8-3.05 kg in accordance with European Pharmacopoeia requirements (European Pharmacopoeia. 7-th Edition, July 2010, pp. 162-163) and requirements of WHO Technical Regulations for Vi-polysaccharide vaccines (Requirements for Vi-polysaccharide typhoid vaccine. WHO Technical Report Series No. 840, 1994, Annex 1). After i.v. administration of each preparation, rabbit rectal temperature was measured three times at intervals of 1 hour. A drug was considered to be apyrogenic if total temperature rise did not exceed 1.15° C. The test results are given in Table 3.

2-acLPS *S flexneri* 2a and *S enterica* sv *typhi* O:901, *K. pneumoniae, E. coli* O:55 are highly apyrogenic preparations. In the rabbit pyrogenicity test the apyrogenic doses of administration were 34, 21, 37 and 14 mcg/kg respectively. For the di-acylated S-LPS derivative the pyrogenicity parameter greatly exceeds the requirements of WHO Committee of Experts for the polysaccharide Hib-vaccine (Recommendations for the production and control *Haemophilis influenzae* type b conjugate vaccines. WHO Technical Report Series, No. 897, 2000). 3-acLPS is also apyrogenic product. Apyrogenic doses of administration of 3-acLPS *S. flexneri* 2a and *S. enterica* sv *typhi* O:901, *K pneumoniae, E. coli* O:55 were 0.2; 0.1; 0.1 and 0.1 mcg/kg respectively. Thus 3-acLPS toxicity reduction exceeds the corresponding parameters for 4-acLPS, however inferior to 2-acLPS according to the degree of detoxification.

TABLE 3

The comparative assessment of pyrogenicity of the individual modified S-LPS and combinations thereof of *S. flexneri* 2a, *S. enterica* sv *typhi* O:901, *K. pneumoniae, E. coli* O:55 bacteria

| Preparation | Dose administration (mcg/kg) | Pyrogenicity |
|---|---|---|
| Vi-antigen typhoid vaccine «Vianvac», lot 270 | 0.050 | apyrogenic |
| 2-acLPS *S flexneri* 2a | 34 | apyrogenic |
| 2-acLPS *S. enterica* sv *typhi* O:901 | 21 | apyrogenic |
| 2-acLPS *K. pneumoniae* | 37 | apyrogenic |
| 2-acLPS *E. coli* O:55 | 14 | apyrogenic |
| 3-acLPS *S. flexneri* 2a | 0.15 | apyrogenic |
| 3-acLPS *S. enterica* sv *typhi* O:901 | 0.1 | apyrogenic |
| 3-acLPS *K. pneumoniae* | 0.08 | apyrogenic |
| 3-acLPS *E. coli* O:55 | 0.1 | apyrogenic |
| 4-acLPS *S. flexneri* 2a | 0.025 | apyrogenic |
| 4-acLPS *S enterica* sv *typhi* O:901 | 0.025 | apyrogenic |
| (2-acLPS + 3-acLPS + 4-acLPS) *S. flexneri* 2a at mass ratio 1:1:1 | 0.6 | apyrogenic |
| (2-acLPS + 3-acLPS + 4-acLPS) *S. enterica* sv *typhi* O:901 at mass ratio 1:1:1 | 0.4 | apyrogenic |
| (2-acLPS + 3-acLPS + 4-acLPS) *K. pneumoniae* at mass ratio 1:1:1 | 0.5 | apyrogenic |
| (2-acLPS + 3-acLPS + 4-acLPS) *E. coli* O:55 at mass ratio 1:1:1 | 0.4 | apyrogenic |
| (3-acLPS + 4-acLPS) *S. flexneri* 2a at mass ratio 3:1 | 0.05 | apyrogenic |
| (3-acLPS + 4-acLPS) *S. enterica* sv *typhi* O:901 at mass ratio 3:1 | 0.05 | apyrogenic |
| (2-acLPS + 3-acLPS) *S. flexneri* 2a at mass ratio 1:1 | 0.5 | apyrogenic |
| (2-acLPS + 3-acLPS) *S. enterica* sv *typhi* O:901 at mass ratio 1:1 | 0.5 | apyrogenic |
| (2-acLPS + 4-acLPS) *S. flexneri* 2a at mass ratio 3:1 | 0.55 | apyrogenic |
| (2-acLPS + 4-acLPS) *S. enterica* sv *typhi* O:901 at mass ratio 3:1 | 0.05 | apyrogenic |
| Westphal LPS *S. flexneri* 2a | 0.0001 | apyrogenic |

The parameter of pyrogenicity of 3-acLPS meets the requirements of WHO Committee of Experts for the polysaccharide Hib-vaccine. 4-acLPS *S. flexneri* 2a and *S. enterica* sv *typhi* O:901 are moderately apyrogenic preparations—doses of thereof up to 0.025 mcg/kg are apyrogenic when administered intravenously. Three-component combinations of individual deacylated S-LPS—(2-acLPS+3-acLPS+4-acLPS) of *S. flexneri* 2a and *S. enterica* sv *typhi* O:901, *K. pneumoniae, E. coli* O:55 bacteria at component mass ratio 1:1:1 have exhibited low pyrogenicity in the rabbit pyrogenicity test. Doses of mentioned combinations of up to 0.6 mcg/kg of rabbit weight are apyrogenic when administered intravenously. Comparative assessment of the most sensitive parameter of in vivo endotoxicity reduction—pyrogenicity—demonstrates the advantage of three component combination compared with 3-acLPS and 4-acLPS which are components of this combination. The synergetic effect of their anti-pyrogenic action is observed at the given mass ratio: mixing of low pyrogenic 2-acLPS with more pyrogenic 3-acLPS and 4-acLPS attenuates about 3-5 times the residual endotoxicity and results in increasing of apyrogenic dose in the combinations, in particular up to 8 times in case of the 4-acLPS. It should be noted that this three-component combination have provided reasonably apparent synergistic effect at any mass ratio of the components containing in the composition, in particular, at the following mass ratio: (45:45:10); (45:10:45); (10:45:45).

Two-component combinations of individual deacylated S-LPS—(2-acLPS+3-acLPS), (2-acLPS+4-acLPS) and (3-acLPS+4-acLPS) of *S. flexneri* 2a and *S enterica* sv *typhi* O:901, *K. pneumoniae, E. coli* O:55 bacteria also have exhibited the synergistic interaction of the components with regard to residual endotoxicity reduction of 3-acLPS or 4-acLPS at any mass ratio of the components containing in the compositions. However two-component combinations of (2-acLPS+3-acLPS) and (2-acLPS+4-acLPS) containing 2-acLPS not less than ½ of total weight (Table 3) have maximum synergistic effect, that allows to admit them the most promising one in terms of safety. So the combination of (2-acLPS+3-acLPS) *S. flexneri* 2a and *S. enterica* sv *typhi* O:901 at component mass ratio 1:1 has exhibited low pyrogenicity (dose administration to rabbits is 1.0 and 0.5 mcg/kg respectively), and combination of (2-acLPS+4-acLPS) at component mass ratio 3:1 has comparable pyrogenicity level. Specific apyrogenic dose of 3-acLPS in two component combination increases in 3-5 times, and of 4-acLPS—up to twice.

D. The immunogenicity of the individual modified S-LPS and combinations thereof.

Two groups of (CBAXC57Bl/6) F1 mice were immunized intraperitoneally (i.p.) with preparations of the individual modified S-LPS—2-acLPS, 3-acLPS, 4-acLPS and combinations—(2-acLPS+3-acLPS+4-acLPS) in component mass ratio 1:1:1, (3-acLPS+4-acLPS) in component mass ratio 3:2, (2-acLPS+3-acLPS) in component mass ratio 1:1, (2-acLPS+4-acLPS) in component mass ratio 3:1 of *S. flexneri* 2a, *S. enterica* sv *typhi* O:901, *K. pneumoniae, E. coli* O:55 bacteria, and also with LPS, obtained from above-mentioned bacteria by the classic Westphal method at a dose of 25 mcg per mouse.

At day 15 after immunization the animal blood sera samplings were taken to evaluate the S-LPS specific IgG antibody levels by ELISA method. LPS with relevant 0-serotypes were used for the adsorption on microplates. To study secondary immune response the same groups of mice were immunized again at a dose of 25 mcg per mouse a month after primary injection. At day 15 after secondary immunization blood sera samplings were taken again.

Obtained results show that di-acylated derivative of S-LPS from *S. flexneri* 2a and *S. enterica* sv *typhi* O:901, *K. pneumoniae, E. coli* O:55 bacteria is less immunogenic than tri- and tetra-acylated derivatives and induces low primary immune response in laboratory animals (FIG. 8A, 9A, 11A). In addition di-acylated derivative of *K. pneumoniae* induces the highest primary immune response (FIG. 10A). Level of the secondary immune IgG response in laboratory animals after immunization with 2-acLPS *S. flexneri* 2a, *S. enterica* sv *typhi* O:901 and *E. coli* O:55 was significantly higher compared with the primary immune response, however, it was lower in 8.0; 8.0 and 7.4 times compared with the secondary immune response to the 3-acLPS and was lower in 12.0; 11.7 and 10.2 times compared with the secondary immune response to 4-acLPS, isolated from homological bacteria (FIG. 8B, 9B, 11B). At the same time the secondary immune IgG-response to the 2-acLPS *K. pneumoniae* was differed only in 2.4 times compared with those to the 3-acLPS (FIG. 10B).

The levels of IgG antibody production in the primary response to the 3-acLPS *S. flexneri* 2a, *S. enterica* sv *typhi* O:901 and *E. coli* O:55 were lower in 3.0; 1.1 and 3.4 times, respectively, compared with primary response to the 4-acLPS with relevant serotype (FIG. 8A, 9A, 11A). The secondary immune response after immunization of laboratory animals with 3-acLPS *S. flexneri* 2a, *S. enterica* sv *typhi* O:901 and *E. coli* O:55 was high (antibody titer exceeded 1600, 4000, 1800), but at the same time it was slightly lower compared with the response to 4-acLPS with relevant serotype (FIG. 8B, 9B, 11B). 4-acLPS *S. flexneri* 2a, *S enterica* sv *typhi* O:901 and *E. coli* O:55 induced the primary immune response in laboratory animals in 3.0; 1.1 and 3.4 times higher compared with those to the 3-acLPS (FIG. 8A, 9A, 11A). Secondary immune response level after immunization of laboratory animals with 4-acLPS was 1.4; 1.5 and 1.2 times higher compared with those to 3-acLPS with relevant serotype (FIG. 8B, 9B, 1B). A slightly higher immunogenicity of 4-acLPS antigen apparently caused by high degree of acylation of its lipid A and thereby has the pronounced ability to form aggregates compared with the other modified S-LPS, especially compared with 2-acLPS.

Combinations of individual modified S-LPS of endotoxic bacteria demonstrate high immunogenic potential despite of essential modification of the canonical structure of its lipid A domain. So three-component combination (2-acLPS+3-acLPS+4-acLPS) induced the primary immune response to O-antigen of *S. flexneri* 2a and *S. enterica* sv *typhi, K. pneumoniae, E. coli* O:55 at component mass ratio 1:1:1, level of which was rather high and did not differ significantly from the response level to classic Westphal LPS, obtained from relevant bacterial strain (FIG. 8A, 9A, 11A). Therefore the immunogenic potentials of low-endotoxic combined modified S-LPS-immunogen and endotoxic and pyrogenic LPS, prepared by the Westphal method were determined to be approximately equal, that indicates that the combination consists of special high-immunogenic with different degree of acylation associates of modified S-LPS which provided the synergistic effect to enhance of its immunogenic properties.

So three-component combinations of (2-acLPS+3-acLPS+4-acLPS) from *S. flexneri* 2a, *S. enterica* sv *typhi* O:901*, K. pneumoniae* and *E. coli* O:55 bacteria induced the secondary IgG immune response at component mass ratio 1:1:1 after immunization of laboratory animals, which was 32.0; 33.6; 8.0 and 32.0 times higher compared with the response to the 2-acLPS; was 4.0; 4.2; 3.3 and 4.3 times higher compared with the response to the 3-acLPS and was 2.7; 2.8; and 3.1 times higher compared with the response to the 4-acLPS (FIG. 8B, 9B, 11B). At the same time administered dose of the individual modified S-LPS in the composition of these combinations is only 33% (w/w) of dose administered as an appropriate monocomponent. It should be noted that this three-component combination of S-LPS provided more or less pronounced synergistic effect directed to increasing of immunogenicity at any component mass ratio, particularly, at the following mass ratio: (10:45:45); (45:10:45); (45:45:10).

Two-component combinations of the individual modified S-LPS—(2-acLPS+3-acLPS), (2-acLPS+4-acLPS) and (3-acLPS+4-acLPS) of *S. flexneri* 2a and *S. enterica* sv *typhi* O:901, *K. pneumoniae, E. coli* O:55 bacteria also exhibit the synergistic interaction with regard to immunogenicity enhancement at any mass ratio of the containing components. Additionally the highest secondary immune response to *Salmonella* or *Shigella* O-antigens was induced by the combinations of (2-acLPS+3-acLPS) at component mass ratio 1:1, (3-acLPS+4-acLPS) at component mass ratio 3:1 and (2-acLPS+4-acLPS) in component mass ratio 3:1. So IgG-response level was the highest to the combination (3-acLPS+4-acLPS) at component mass ratio 3:1 of *S. flexneri* 2a and for the combination (2-acLPS+3-acLPS) at component mass ratio 1:1 of *S. enterica* sv *typhi* O:901 (FIG. 8B, 9B). It should be noted that three-component combination provides more pronounced synergistic effect compared with to two-component combination. So slightly higher IgG-response levels were determined after immunization with three-component combination in the comparative immunogenicity study of the three-component combination from *S. flexneri* 2a and *S. enterica* sv *typhi* O:901 bacteria in component mass ratio 1:1:1 and two-component low-pyrogenic homologous of O-antigen combinations of (2-acLPS+3-acLPS), (3-acLPS+4-acLPS) and (2-acLPS+4-acLPS) at component mass ratio 1:1, 3:1 3:1, respectively (FIG. 8A, 9A).

Thus the immunogenicity of combinations of the modified S-LPS is determined by composition, amount and mass ratio of components. Three-component combination can be considered the most effective combination. In the meantime the immunogenicity of combinations of the modified S-LPS is also defined by the structure (serotype) of O-antigen of enterobacteria. For the number of serotypes the high rise of the IgG antibodies can be achieved also using two-component low-pyrogenic combinations of the modified S-LPS.

Example 3

Vaccines Containing Modified S-LPS of Endotoxic Bacteria and Combinations Thereof

A. Use of the Modified S-LPS and Combinations Thereof in the Manufacture of the Unconjugated Vaccine (Medicament)

Preparation of unconjugated vaccine includes the synthesis of the individual di-, tri- and tetra-acylated derivatives of S-LPS and combinations as per Examples 2A, 2B and the subsequent aseptic filling of vials or syringes with solution containing the active substance and pharmaceutically acceptable special additives, which may be pH stabilizers, preservatives, adjuvants, isotonizing agents or combinations thereof. Vaccination dose contains: unconjugated form of the modified S-LPS or combination of unconjugated forms of the modified S-LPS in amount from 0.010 mg to 10 mg; phenol (preservative), not more than 0.75 mg, with addition of sodium chloride—4.150 mg, dibasic sodium phosphate—0.052 mg and monobasic sodium phosphate—0.017 mg; sterile pyrogen-free water for injection—0.5 mL (PA 42-2620-97, EP IV 2002).

B. Pyrogenicity of the Unconjugated Vaccine

Pyrogenicity of vaccine containing 2-acLPS, 3-acLPS, combination of (2-acLPS+3-acLPS+4-acLPS) at component mass ratio 1:1:1*, S. flexneri* 2a; 2-acLPS, 3-acLPS, combination of (2-acLPS+3-acLPS+4-acLPS) at component mass ratio 1:1:1, *S. enterica* sv *typhi* O:901 was determined and compared with pyrogenicity of the commercial Vi-antigen vaccine. All given vaccine preparations were apyrogenic at a dose of 0.050 mcg/kg per rabbit weight. Test results are provided in Table 4.

TABLE 4

Pyrogenicity of the unconjugated vaccine containing the modified S-LPS and combinations of the modified S-LPS of S. flexneri 2a and S. enterica sv typhi O:901 bacteria at a dose 0.050 mcg/kg per rabbit weight

| Preparation | Temperature increase, in ° C. | Pyrogenicity |
|---|---|---|
| Vi-antigen typhoid vaccine «Vianvac» 152 | (0.3; 0.2; 0.0) Σ: 0.5 | apyrogenic |
| Dysentery vaccine containing 2-acLPS S. flexneri 2a | (0.2; 0.1; 0.0) Σ: 0.3 | apyrogenic |
| Dysentery vaccine containing 3-acLPS S. flexneri 2a | (0.2; 0.2; 0.1) Σ: 0.5 | apyrogenic |
| Dysentery vaccine containing combination of (2-acLPS + 3-acLPS + 4-acLPS) S. flexneri 2a at mass ratio 1:1:1 | (0.2; 0.2; 0.1) Σ: 0.5 | apyrogenic |
| Typhoid vaccine containing 2-acLPS S. enterica sv typhi O:901 | (0.1; 0.2; 0.1) Σ: 0.4 | apyrogenic |
| Typhoid vaccine containing 3-acLPS S. enterica sv typhi O:901 | (0.2; 0.2; 0.2) Σ: 0.6 | apyrogenic |
| Typhoid vaccine containing of combination of (2-acLPS + 3-acLPS + 4-acLPS) S. enterica sv typhi O:901 at mass ratio 1:1:1 | (0.1; 0.0; 0.3) Σ: 0.4 | apyrogenic |

C. Protective Properties of the Unconjugated Vaccine

The evaluation of protective properties of the vaccines containing combination of the modified S-LPS was conducted in experimental models of dysentery infection (Sereny test; Sereny B. A new method for the measurement of protective potency of disentery vaccines. Acta Microbiol., Acad. Sci. Hung., 1962, v. 9, pp. 55-60) and typhoid infection (active mouse-protection test). To study the formation of protective shigella mucosal immunity in guinea pigs, laboratory animals weighing 200-250 g were immunized twice with an interval of 10 days subcutaneously (s.c.) in the back region with vaccine, including 3-acLPS or combination of (2acLPS+3acLPS+4acLPS) at mass ratio 1:1:1 or combination of (2-acLPS+3-acLPS) at mass ratio 3:1 of S. flexneri 2a at a doses of 25 and 50 mcg per animal. Control animals were given saline instead of the vaccine preparation. Ten days after the last immunization, Dysentery keratoconjunctivitis (Sereny test) was induced in the experimental and control animals by introduction into the eye conjunctiva cell suspension of virulent strain of S. flexneri 2a at a dose, close to the $ID_{100}$ ($10^9$ cells), and at a dose close to the $2ID_{100}$ ($2\times10^9$ cells), in 30 mcL of sterile saline. All animals in the control group, infected with a dose of $2\times10^9$ cells, and 90% of animals in the control group, infected with a dose of $10^9$ cells, developed dysentery keratoconjunctivitis (Table 5).

Immunization with vaccine, including combination of (2-acLPS+3-acLPS+4-acLPS) S. flexneri 2a in mass ratio 1:1:1, at a dose of 25 mcg, provided eye protection rate in 75% of experimental animals infected at a dose of $10^9$ cells; eye protection rate was 60% when they were infected at a dose of $2\times10^9$ cells. Immunization with vaccine at a dose of 50 mcg provided eye protection rate in 70% of experimental animals infected at a dose of $10^9$ cells; eye protection rate was 60% when they were infected at a dose of $2\times10^9$ cells.

The eye protection rate from experimental dysentery infection when guinea pigs were immunized with vaccines, including 3-acLPS or combination of (2-acLPS+3-acLPS) at mass ratio 3:1 of S. flexneri 2a bacteria also varied from 55 to 75%.

Therefore the pronounced mucosal antidysentery immunity was registered after s.c. immunization of animals with vaccine containing 3-acLPS or combination of (2-acLPS+3-acLPS+-4acLPS) at mass ratio 1:1:1 or combination of (2-acLPS+3-acLPS) at mass ratio 3:1 of S. flexneri 2a.

TABLE 5

The protective mucosal immunity in guinea pigs as a result of the systemic immunization with vaccines containing the modified S-LPS and the combinations of the modified S-LPS of S.flexneri 2a bacteria

| Preparation | Preparation dose, mcg per animal | Infection dose (No. of cells in 30 mcL of saline solution) | No. of infected animals | No. of infected animal eyes | No. of eyes with keratoconjuncti- vitis | No. of eyes protected from keratoconjuncti- vitis | Eye protection rate, % |
|---|---|---|---|---|---|---|---|
| Vaccine, containing (2-acLPS + 3-acLPS + 4-acLPS) at mass ratio 1:1:1 | 25 | $10^9$ | 10 | 20 | 5 | 15 | 75 |
| | 25 | $2 \times 10^9$ | 10 | 20 | 8 | 12 | 60 |
| | 50 | $10^9$ | 10 | 20 | 6 | 14 | 70 |
| | 50 | $2 \times 10^9$ | 10 | 20 | 8 | 12 | 60 |
| Vaccine, containing (2-acLPS + 3-acLPS) at mass ratio 3:1 | 25 | $10^9$ | 10 | 20 | 5 | 15 | 75 |
| | 25 | $2 \times 10^9$ | 10 | 20 | 7 | 13 | 65 |
| | 50 | $10^9$ | 10 | 20 | 6 | 14 | 70 |
| | 50 | $2 \times 10^9$ | 10 | 20 | 9 | 11 | 55 |
| Vaccine, containing 3-acLPS | 25 | $10^9$ | 10 | 20 | 7 | 13 | 65 |
| | 25 | $2 \times 10^9$ | 10 | 20 | 6 | 14 | 70 |
| | 50 | $10^9$ | 10 | 20 | 7 | 13 | 65 |
| | 50 | $2 \times 10^9$ | 10 | 20 | 8 | 12 | 60 |
| Control | — | $10^9$ | 10 | 20 | 19 | 1 | 5 |
| | — | $2 \times 10^9$ | 10 | 20 | 20 | 0 | 0 |

To study protective typhoid immunity the test group of (CBAXC57Bl/6) F1 mice was intraperitoneally immunized with dose gradient of vaccine, including 3-acLPS *S. enterica* sv *typhi* O:901 and also with vaccine containing combination of (2-acLPS+3-acLPS+4-acLPS) *S. enterica* sv *typhi* O:901 at mass ratio 1:1:1. Control animals were given saline. After 12-14 days both animal groups were i.p. infected with 1000 cells (m.c.) of virulent typhoid strain of *S. enterica* sv *typhi* Ty2 No. 4446 at a dose of 80 $LD_{50}$ in sterile saline containing 5% (w/w) mucin type III (Sigma, USA) as per Joo's protocol (Joo I., Pusztai Z., Juhasz V. P. Mouse-protective ability of the international reference preparations of typhoid vaccine. Z. Immun. Forsch. exp. Ther., 1968, v. 135, pp. 365-72). Animal survival rate in both groups was registered for 3-5 days.

TABLE 6

The Comparative characteristic of protective properties of vaccines, including the modified S-LPS or combination of the modified S-LPS of *S. enterica* sv typhi O:901 bacteria, and typhoid vaccine Typhim Vi

| Preparation | Dose, mcg per mouse | Immunisation method | No of mice in group | Mouse survival rate after immunization and infection with *S. enterica* sv typhi Ty2 No. 4446 in 5% mucin 1000 cells (80 $LD_{50}$) |
|---|---|---|---|---|
| Vaccine, containing 3-acLPS *S. enterica* sv typhi O:901 | 25 | i.p. | 10 | 10/10 |
| | 2.5 | i.p. | 10 | 10/10 |
| | 0.25 | i.p. | 10 | 10/10 |
| | 0.025 | i.p. | 10 | 8/10 |
| | 0.0025 | i.p. | 10 | 9/10 |
| | 0.00025 | i.p. | 10 | 8/10 |
| Vaccine, containing (2-acLPS + 3-acLPS + 4-acLPS) *S. enterica* sv typhi O:901 at mass ratio 1:1:1 | 25 | i.p. | 10 | 10/10 |
| | 2.5 | i.p. | 10 | 10/10 |
| | 0.25 | i.p. | 10 | 10/10 |
| | 0.025 | i.p. | 10 | 10/10 |
| | 0.0025 | i.p. | 10 | 8/10 |
| | 0.00025 | i.p. | 10 | 8/10 |
| Typhim Vi | 25 | i.p. | 10 | 10/10 |
| | 2.5 | i.p. | 10 | 10/10 |
| | 0.25 | i.p. | 10 | 10/10 |
| | 0.025 | i.p. | 10 | 10/10 |
| | 0.0025 | i.p. | 10 | 10/10 |
| | 0.00025 | i.p. | 10 | 8/10 |
| Control infection $LD_{50}$ = 12.5 cells | 1 cell | | | 8/10 |
| | 10 cells | | | 6/10 |
| | 100 cells | | | 0/10 |
| | 1000 cells | | | 0/10 |

As it follows from Table 6, test of active mice protection displayed the essential protective efficiency for the claimed vaccines. So vaccine, including the combination of (2-acLPS+3-acLPS+4-acLPS) *S. enterica* sv *typhi* O:901 at mass ratio 1:1:1 has protective efficiency comparable with vaccine preparation TYPHIM-Vi in test in mice and meets the requirements of quantitative standardization of protective activity for the typhoid vaccines.

D. Anti-Shock Activity of Unconjugated Vaccine

Animal protection from endotoxic shock was performed by prophylactic i.p. immunization of test groups of (CBAXC57Bl/6)F1 mice with vaccine, including combination of (2-acLPS+3-acLPS+4-acLPS) *S. sonnei* at mass ratio 1:1:1 and vaccine containing combination of (2-acLPS+3-acLPS+4-acLPS) *E. coli* O:55 at mass ratio 1:1:1, at doses of 50, 100 and 200 mcg/per mouse (that are equivalent to 2.5; 5 and 10 mg/kg, respectively) in 0.5 mL 0.9%-sodium chloride solution 72 hours prior to endotoxic shock induction. The endotoxic shock was induced by i.p. administration of standard endotoxin of *E. coli* O:55 (Sigma-Aldrich, USA) at a dose of 2 mg/per mouse (100 mg/kg), that is approximately 4 LD100. Control group was i.p. administered of 0.5 mL saline by the same scheme. Animal survival rate was evaluated for 3 days after injection of endotoxin (Table 7).

TABLE 7

The survival rate of (CBA × C57B1/6)F1 mice, immunized by vaccines containing combinations of the modified S-LPS of *S.sonnei* and *Escherichia coli* O:55, in the induction of endotoxic shock by i.p. injection of 4 LD100 of LPS *E.coli* O:55

| Preparation | Dose, mcg per animal | No of mice in group | Death of mice at time intervals (hours) | | | Survival rate, % |
|---|---|---|---|---|---|---|
| | | | 0-24 | 24-48 | 48-72 | |
| Vaccine, containing (2-acLPS + 3-acLPS + 4-acLPS) *S.* at mass ratio 1:1:1 | 50 | 5 | 3 | — | — | 40 |
| | 100 | 5 | 1 | — | — | 80 |
| | 200 | 5 | — | 1 | — | 80 |
| Vaccine, containing (2-acLPS + 3-acLPS + 4-acLPS) *E. coli* O:55 at mass ratio 1:1:1 | 50 | 5 | 3 | 1 | — | 20 |
| | 100 | 5 | 2 | 1 | — | 40 |
| | 200 | 5 | 1 | 1 | — | 60 |
| Control | 0 | 5 | 5 | — | — | 0 |

As it follows from Table 7 despite of reduced endotoxicity the claimed vaccines are effective prophylactic preparations at a dose of 100 and 200 mcg/mouse which provides 80% and 40-60%, respectively, survival rate of experimental animals associated with massive (4 LD100) endotoxic load and as a result, the correction of pathogenic mechanism of endotoxic shock. At the same time vaccine, including combination of the modified S-LPS *S. sonnei* had more pronounced anti shock activity than analogous *E. coli* O:55 vaccine.

Animal protection from septic shock was performed by prophylactic i.p. immunization of test groups of (CBAXC57Bl/6)F1 mice with vaccine, including the combination of (2-acLPS+3-acLPS+4-acLPS) *S. sonnei* at mass ratio 1:1:1 and vaccine containing combination of (2-acLPS+3-acLPS+4-acLPS) *E. coli* O: 55 at mass ratio 1:1:1, in a dose of 10 and 50 mcg per mouse (that are equivalent to 0.5 and 2.5 mg/kg, respectively) twice with an interval of 30 days prior to simulation of septic shock. Septic shock simulation was conducted after 18 days after secondary immunization. Control group consisted of intact postoperative animals (Table 8).

Septic shock (experimental peritonitis) simulation was conducted by cecal ligation and puncture procedure (CLP-model). Test and control mice groups were anesthetized by general anaesthesia, peritoneum was opened, cecum and appendix were eviscerated. The cecum was ligated in the area adjacent to appendix and punctured twice through by 22G needle. The contents of the cecum were extruded through the formed holes for contamination of the peritoneal cavity of gut contents, then organs were returned back to abdomen and abdominal cavity was stitched.

TABLE 8

Septic shock correction in mice immunized by vaccines containing the combinations
of the modified S-LPS of S. sonnei and E. coli O:55, during the
CLP-procedure on the day 8 after the primary immunization

| Preparation | Dose, mcg per mouse | Death of the first animal (hours) | Death of the last animal (hours) | Suppression of the peritonitis development Δt (hours) | Increase of survival rate under sepsis Δt (hours) |
|---|---|---|---|---|---|
| Vaccine containing (2-acLPS + 3-acLPS + 4-acLPS) S. sonnei at mass ratio 1:1:1 | 10 50 | 66 48 | 168 165 | 30 12 | 36 33 |
| Vaccine containing (2-acLPS + 3-acLPS + 4-acLPS) E. coli O:55 at mass ratio 1:1:1 | 10 50 | 54 42 | 156 150 | 18 6 | 24 18 |
| Control | 0 | 36 | 132 | — | — |

As it follows from Table 8, immunization of animals with the claimed vaccines at a dose of 10 mcg/mouse is considered to be more effective providing the suppression of experimental peritonitis development (for 30 and 18 hours compared with control group) and increase the survival rate under sepsis (for 36 and 24 hours compared with control group).

E. Safety of Unconjugated Vaccine

Dysentery vaccine, including the combination of (2-acLPS+3-acLPS+4-acLPS) S. flexneri 2a in component mass ratio 1:1:1, and vaccine comprising the combination (2-acLPS+3-acLPS+4-acLPS) S. enterica sv typhi O:901 in component mass ratio 1:1:1, at a dose of 50 mcg of antigen containing in 0.5 mL phenol-phosphate buffer solution as a solvent and product for comparison—typhoid Vi-antigen vaccine "Vianvac", at a dose of 25 mcg, were injected once subcutaneously in the upper third of the shoulder to three groups of 20 adult volunteers. Temperature reactions to the drug injection, general side effects and local reactions of volunteers were studied for the first three days after immunization. Vaccine containing combination of the modified S-LPS of S. flexneri 2a has shown high safety profile for adult volunteers. Temperature reactions at the 37.1-37.5° C. range were found in only 5% of volunteers, higher temperature reactions and general side effects were absent; local reaction (pain at the injection site) was detected only in one volunteer (Table 9). Temperature reactions in the 37.1-37.5° C. range were found in only 10% of volunteers immunized with vaccine containing combination of the modified S-LPS S. enterica sv typhi O:901 or typhoid Vi-antigen vaccine "Vianvac" (Table 9).

TABLE 9

Vaccine safety containing combination of the modified S-LPS S. flexneri 2a
and S. enterica sv typhi O:901, under immunization of the adult volunteers

| Reactions on vaccine administration | Vaccine containing (2-acLPS + 3-acLPS + 4-acLPS) S. flexneri 2a at mass ratio 1:1:1, at a dose of 50 mcg per human (n = 20) | Vaccine containing (2-acLPS + 3-acLPS + 4-acLPS) S. enterica sv typhi O:901 at mass ratio 1:1:1, at a dose of 50 mcg per human (n = 20) | typhoid Vi-antigen vaccine "Vianvac" (lot 193), at a dose of 25 mcg per human (n = 20) |
|---|---|---|---|
| Temperature reactions (37.1-37.5° C.) | found in 5% of volunteers | found in 10% of volunteers | found in 10% of volunteers |
| Temperature reactions (37.6-38.5° C.) | absent | Absent | Absent |
| Temperature reactions (38.5° C. and up) | absent | Absent | Absent |
| General side effects | absent | Absent | Absent |
| Local reactions (pain) | 1 case | 2 cases | 1 case |

Production of proinflammatory cytokines was studied to evaluate safety of the claimed vaccines when it were administered parenterally (subcutaneously) to human. Vaccines including the combinations of modified S-LPS *S. flexneri* 2a and *S. enterica* sv *typhi* O:901, at a dose of 50 mcg of antigen, containing in 0.5 mL phenol-phosphate buffer solution as a solvent, were injected once subcutaneously to volunteers in the outer surface of the upper third of the shoulder.

After immunization volunteers were under the supervision of a doctor for 5 days. On the first day of supervision they underwent medical examinations at 2, 4, 6 and 24 hours after injection of drug preparations. To study cytokine status, the blood samples were taken from volunteer's veins before the injection of the claimed vaccines (0 hour) and at 2, 4 and 6 hours after administration. According to literature data TNF-α, IL-113, IL-6 arrange triad of proinflammatory cytokines—basic mediators of sepsis (Casey L. C., Balk R. A., Bone R. C. Plasma cytokine and endotoxin levels correlate with survival in patients with the sepsis syndrome. Ann. Intern. Med., 1993; 119: 771-78.). I.v. administration of Westphal LPS *E. coli* at a dose of 0.06-0.2 ng/kg provides the rise of level of circulating TNF-α and IL-6 in 2-100 times (Taudorf S., Krabbe K. S., Berg R. M. G., Pedersen B. K., Moller K. Human models of low-grade inflammation: bolus versus continuous infusion of endotoxin. Clin. Vaccine Immunol., 2007; 14(3): 250-55), whereas in the experiment by immunization to volunteers with vaccine containing combination of the modified S-LPS of *S. flexneri* 2a and with typhoid vaccine containing combination of the modified S-LPS of *S. enterica* sv *typhi* O:901, in a dose of 50 mcg (that is equivalent to 0.8-1 mcg/kg), proinflammatory cytokine concentrations were low and did not significantly differ from those in serum taken from volunteers before vaccine injection (Table 10). At the same time TNF-α concentration increased a little at 2 hours, IL-6 at 4 hours after administration of the claimed vaccines and IL-1β concentration did not change practically and stayed at the basal level.

TABLE 10

The profiles of proinflammatory cytokines in volunteer's blood serum after immunization with dysentery vaccine containing combination of the modified S-LPS *S. flexneri* 2a and typhoid vaccine containing combination of the modified S-LPS *S. enterica* sv typhi O:901

| | Parameter Mean value ± standard deviation (pg/mL) | |
|---|---|---|
| Time after vaccine injection (hours) | Dysentery vaccine, containing (2-acLPS + 3-acLPS + 4-acLPS) *S. flexneri* 2a at mass ratio 1:1:1, at a dose of (50 mcg/0.5 mL) | Typhoid vaccine, containing (2-acLPS + 3-acLPS + 4-acLPS) *S. enterica* sv typhi O:901 2a at mass ratio 1:1:1, at a dose of (50 mcg/0.5 mL) |
| | TNF-α | |
| 0 | 11.23 ± 2.2 | 13.86 ± 1.6 |
| 2 | 17.95 ± 4.34 | 17.35 ± 1.78 |
| 4 | 13.54 ± 4.18 | 11.20 ± 205 |
| 6 | 11.76 ± 0 | 10.08 ± 0 |
| | IL-1β | |
| 0 | 0.005 ± 0.009 | 0.05 ± 0 |
| 2 | 0 | 0.2 ± 0 |
| 4 | 1.49 ± 0.51 | 0.2 ± 0 |
| 6 | 0 | 0.05 ± 0 |
| | IL-6 | |
| 0 | 1.27 ± 0.91 | 0.23 ± 0.16 |
| 2 | 1.96 ± 1.53 | 2.66 ± 1.5 |
| 4 | 6.06 ± 2.1 | 2.21 ± 0.99 |
| 6 | 2.59 ± 0 | 1.52 ± 0 |

F. Immunogenicity of Unconjugated Vaccine

Volunteer's immune response was investigated after single subcutaneously immunization in the upper third of the shoulder of test groups of 20 adult volunteers with vaccines including the modified S-LPS and combination of the modified S-LPS *S. flexneri* 2a, and also vaccine containing the combination of the modified S-LPS *S. enterica* sv *typhi* O:901, at a dose of 50 mcg of antigen, containing in 0.5 mL phenol-phosphate buffer solution as a solvent. Secondary immunization was performed in the same manner after 30 days after primary immunization. Blood sera for research were taken from volunteers before vaccination and after 30 days after primary and secondary vaccination, respectively.

Main classes of specific anti-LPS *S. flexneri* 2a and *S. enterica* sv *typhi* O:901 antibodies were determined by ELISA method using isotype-specific anti-IgA, anti-IgG and anti-IgM antibodies conjugated with HRP. Vaccine immunogenicity was evaluated by 4-fold-or-greater rise of levels of LPS-specific antibodies in immune sera-seroconversion compared with the background sera levels.

TABLE 11

The immunogenicity of vaccines containing the modified S-LPS *S. flexneri* 2a and combinations of the modified S-LPS *S. flexneri* 2a and *S. enterica* sv typhi O:901 (primary vaccination)

| | | | Day 30 after primary vaccination | | |
|---|---|---|---|---|---|
| Preparation | Immunization dose, mcg per human | No of volunteers in group | % volunteers with seroconversion IgA ≥ 4 | % volunteers with seroconversion IgG ≥ 4 | % volunteers with seroconversion IgM ≥ 4 |
| Vaccine, containing 3-acLPS *S. flexneri* 2a | 50 | 20 | 40 | 40 | 0 |
| Vaccine, containing (2-acLPS + 3-acLPS + 4-acLPS) *S. flexneri* 2a at mass ratio 1:1:1 | 50 | 20 | 80 | 50 | 0 |

TABLE 11-continued The immunogenicity of vaccines containing the modified S-LPS *S. flexneri* 2a and combinations
of the modified S-LPS *S. flexneri* 2a and *S. enterica* sv typhi O:901 (primary vaccination)

| Preparation | Immunization dose, mcg per human | No of volunteers in group | Day 30 after primary vaccination % volunteers with seroconversion IgA ≥ 4 | % volunteers with seroconversion IgG ≥ 4 | % volunteers with seroconversion IgM ≥ 4 |
|---|---|---|---|---|---|
| Vaccine, containing (2-acLPS + 3-acLPS + 4-acLPS) *S. enterica* sv typhi O:901 at mass ratio 1:1:1 | 50 | 20 | 70 | 80 | 55 |

TABLE 12

The immunogenicity of vaccines containing the modified S-LPS *S. flexneri* 2a and combination of modified S-LPS *S. flexneri* 2a and *S. enterica* sv typhi O:901 (secondary vaccination)

| Preparation | Immunization dose, mcg per human | No of volunteers in group | Day 30 after secondary vaccination % volunteers with seroconversion IgA ≥ 4 | % volunteers with seroconversion IgG ≥ 4 | % volunteers with seroconversion IgM ≥ 4 |
|---|---|---|---|---|---|
| Vaccine, containing 2-acLPS *S. flexneri* 2a | 50 | 20 | 40 | 40 | 10 |
| Vaccine, containing 3-acLPS *S. flexneri* 2a | 50 | 20 | 40 | 40 | 15 |
| Vaccine, containing (2-acLPS + 3-acLPS + 4-acLPS) *S. flexneri* 2a at mass ratio 1:1:1 | 50 | 20 | 80 | 70 | 20 |
| Vaccine, containing (2-acLPS + 3-acLPS + 4-acLPS) *S. enterica* sv typhi O:901 at mass ratio 1:1:1 | 50 | 20 | 75 | 70 | 60 |

It was found that high levels of specific IgA-antibodies were observed either by detection frequency or final titer after primary and secondary immunization of volunteers with vaccines containing combinations of the modified S-LPS *S. flexneri* 2a and *S. enterica* sv *typhi* O:901 (Table 11, 12).

The frequency of detection of 4-fold and more rise of IgA anti-LPS antibody titers after immunization with vaccine containing combination of the modified S-LPS *S. flexneri* 2a was 80% after primary and secondary immunization, the maximum detection frequency of 4-fold Ig seroconversion of IgG antibodies in 70% cases was detected after secondary immunization.

4-fold and more titer rise of IgA anti-LPS antibodies after primary and secondary immunization with vaccine containing combination of the modified S-LPS *S. enterica* sv *typhi* O:901 was found in 70 and 75% of volunteers respectively, the maximum detection frequency of 4-fold and more seroconversions of IgG antibodies in vaccinated volunteers was 80% after primary immunization.

4-fold and more titer rise of specific IgA antibodies after primary and secondary immunization with vaccine containing 3-acLPS *S. flexneri* 2a was found in 40 and 40% of volunteers respectively. Frequency of 4-fold and more seroconversions of IgG antibodies was 40 and 40% in vaccinate volunteers after primary and secondary immunization with 3-acLPS *S. flexneri* 2a, respectively.

Level increasing of LPS-specific IgM-antibodies in volunteers immunized with vaccines including both combinations of the modified S-LPS *S. flexneri* 2a and 3-acLPS *S. flexneri* 2a was negligible and gave rise after secondary immunization to 10 and 15% of 4-fold and more seroconversions, respectively.

Frequency increasing of seroconversion of IgM-antibodies in volunteers immunized by vaccine containing combination of the modified S-LPS *S. enterica* sv *typhi* O:901 was significant and was 55% after primary immunization and 60% after secondary immunization.

Secondary immune response was registered in volunteers immunized by vaccine including 2-acLPS *S. flexneri* 2a, as rising of IgA and IgG antibodies to LPS *S. flexneri* 2a.

Therefore trial results have proved high immunogenicity for human of dysentery vaccine, containing combination of the modified S-LPS *S. flexneri* 2a and typhoid vaccine containing combination of the modified S-LPS *S. enterica* sv *typhi* O:901. Specific antibodies were presented by the classes of IgA- and IgG-antibodies, the most important for mucosal immunity.

G. Use of Combinations of the Modified S-LPS as Immunostimulating Carrier in the Manufacture of Conjugated Vaccine (Medicament)

Combination of (2-acLPS+3-acLPS+4-acLPS) at component mass ratio 1:1:1 was obtained from *S. enterica* sv *typhi*

O:901 bacteria according to Examples 2A and 2B. To generate active functional groups in modified S-LPS, obtained combination was subjected to partial periodate oxidation followed by oxidation of generated aldehyde groups to carboxylic ones. Then partially oxidized modified S-LPS can be conjugated with vaccine antigens by any of known methods. This study used method of conjugation with polysaccharide antigen—capsule Vi-antigen or protein antigen—tetanus toxoid (TT) using 1-ethyl-3-(3-dimethylaminopropyl) carbodiimide (EDC).

Conjugation of partially oxidized combination of the modified S-LPS *S. enterica* sv *typhi* O:901 with Vi-antigen or TT was conducted in 0.2M sodium chloride solution in the presence of EDC for 4-18 hours maintaining pH value 5.6 by pH-stat. Conjugates were purified from nonconjugated initial biopolymers and low molecular impurities on Sepharose CL-6B column using 0.2M sodium chloride solution as an eluent. Fractions, containing conjugates and eluted near the column void volume, were combined for subsequent filling in sterile vials with addition of pharmaceutically suitable special additives, as which used pH stabilizers or preservatives, or adjuvants, or isotonizing agents or combinations thereof.

The vaccine conjugate of combination of the modified S-LPS *S. enterica* sv *typhi* O:901 with Vi-antigen contained 50% (w/w) serological active Vi-antigen determined by ELISA method.

But the vaccine conjugate of the same combination with TT contained 40% (w/w) protein mass, determined by Bradford method (Bradford M. M. A rapid and sensitive method for the quantitation of microgram quantities of protein utilizing the principle of protein-dye binding. Anal. Biochem. 1976, v. 72, pp. 248-54).

One vaccination dose of conjugated vaccine contains: conjugate of combination of the modified S-LPS, from 0.010 to 0.200 mg; phenol (preservative), not more than 0.75 mg, with addition of sodium chloride—4.150 mg, dibasic sodium phosphate, 0.052 mg and monobasic sodium phosphate, 0.017 mg; sterile pyrogen-free water for injection, 0.5 mL (PA 42-2620-97, EP IV 2002).

H. Immunogenicity of Conjugated Vaccines

The mouse immune response was studied for the conjugates of polysaccharide Vi-antigen and protein TT with immunostimulating carrier—combination of (2-acLPS+3-acLPS+4-acLPS) *S. enterica* sv *typhi* O:901 at component mass ratio 1:1:1.

Groups of (CBAXC57Bl/6) F1 mice were i.p. immunized by abovementioned Vi-antigen conjugate and pure Vi-antigen at a dose of 25 mcg of polysaccharide per mouse. The conjugate induced humoral immune response and at 15 day after its single injection 5.8-fold rise of IgG antibody amount was detected in animal peripheral blood sera compared with the response of pure Vi-antigen by ELISA method. (FIG. 12A).

To study secondary immune response the same groups of mice were re-immunized with the indicated vaccine at a dose of 25 mcg of polysaccharide per mouse one month after primary administration. On day 15 after re-immunization with conjugate 8.2-fold rise of IgG anti Vi-antibody amount was registered. (FIG. 12B).

Conjugate of protein TT with immunostimulating carrier—combination of the modified S-LPS *S. enterica* sv *typhi* O:901 and pure TT was also administered i.p. to groups of (CBAXC57Bl/6)F1 mice at a dose of 20 mcg of protein per mouse. Conjugate induced humoral immune response after single injection and on 15 day 3-fold rise of IgG antibody amount was determined in animal peripheral blood sera compared with the response of pure TT (FIG. 12A).

To study secondary immune response the same groups of mice were re-immunized with the indicated vaccine at a dose of 20 mcg of protein per mouse after month after primary administration. On day 15 after re-immunization with conjugate 6.4-fold rise of IgG anti-TT antibody amount was registered. (FIG. 12B).

It should be noted that O-specific antibody levels to immunostimulating carrier combination of the modified S-LPS *S. enterica* sv *typhi* O:901, induced by conjugate with TT, also rose: at primary response—in 3.2 times and at secondary one—1.5 times (FIGS. 12A and B). Therefore additional rise of immune response was observed both for protein antigen and for carrier when administered of S-LPS conjugate with protein carrier.

I. Multivalent Dysentery-Typhoid-*Escherichia coli* Vaccine

To prepare polyvalent vaccine substance against *Shigella flexneri* or *sonnei* shigelosis, typhoid fever and enterohaemorrhagic *E. coli* O:55 infection equal mass fractions of combination (2-acLPS+3-acLPS+4-acLPS) substance at component ratio 1:1:1 of serotype *S. flexneri* 2a, *S. sonnei, S. enterica* sv *typhi* O:901 and *E. coli* O:55, obtained as per Examples 2A and 2B were dissolved in pyrogen-free water. Final vaccine form was prepared according to Example 3A.

The immunogenicity of multivalent Dysentery—Typhoid-*Escherichia coli* vaccine was determined by tests in (CBAXC57Bl/6)FI mice, which were immunized i.p. by polyvalent vaccine at a dose of 100 mcg per mouse. Components of polyvalent vaccine—combination (2-acLPS+3-acLPS+4-acLPS) at ratio 1:1:1 *S. flexneri* 2a or *S. sonnei* or *S. enterica* sv *typhi* O:901 or *E. coli* O:55 were also injected separately to different mouse groups at a dose of 25 mcg per mouse. On 15 day animal blood sera samplings were taken. To study secondary immune response the same groups of mice were re-immunized by the indicated drug preparations at a dose of 100 or 25 mcg per mouse one month after primary injection. On day 15 after secondary immunization animal blood sera samplings were taken. Multivalent vaccine induced immune response after primary and secondary immunization. At the same time multivalent vaccine exceeded IgG antibody titer for the all its individual components—typhoid *S. enterica* sv *typhi* O:901, dysentery *S. flexneri* 2a and dysentery *S. sonnei* and *Escherichia coli* O:55 up to level compared with response level after separate administration of the corresponding component at a dose of 25 mcg (FIG. 13A, B).

Thus multivalent Dysentery-Typhoid-*Escherichia coli* vaccine simultaneously induces immune response in mice to the modified S-LPS antigens, isolated from 4 bacteria strains, relating to three different families of endotoxic bacteria.

Example 4

Pharmaceutical Composition Containing the Modified S-LPS and Combinations of them A. Use of the Modified S-LPS and Combinations of them in the Manufacture of the Pharmaceutical Composition (Medicament)

Preparation of pharmaceutical composition includes the synthesis of the modified S-LPS and combinations thereof as per Examples 2A and 2B with the subsequent aseptic filling of vials or syringes with solution containing the active substance and pharmaceutically suitable special additives, as which may be used pH stabilizers, preservatives, adjuvants, isotonizing agents or combinations thereof. Therapeutic dose of pharmaceutical composition contains: combination of (2-acLPS+3-acLPS+4-acLPS) at component mass ratio 1:1:1, *S. enterica* sv *typhi* O:901 *salmonella*, from 0.010 to 50.000 mg; phenol (preservative), not more than 0.75 mg, with addition of sodium chloride—4.150 mg and monobasic sodium phosphate, 0.017 mg; sterile pyrogen-free water for injection, 0.5 mL (PA 42-2620-97, EP IV 2002).

B. Antiviral Action of Pharmaceutical Composition

Antiviral action of pharmaceutical composition containing combination of (2-acLPS+3-acLPS+4-acLPS) at component mass ratio 1:1:1 from *S. enterica* sv *typhi* O:901 *salmonella* was studied in white mice. The test and control groups of male mice (per 10 animals in group) weighing 18-20 g were infected with virulent influenza A H1N1 virus at a dose of LD100, after this animals in test groups were treated by i.p. daily administration of the drug preparation composed of combination of (2-acLPS+3-acLPS+4-acLPS) at component mass ratio 1:1:1 *S. enterica* sv *typhi* O:901, at a dose of 100 mcg per animal. Control groups of mice were given saline solution in similar fashion. Animal survival rate was determined for two weeks after infection. Mice survival rate was 0% in control group and 40% in test group (FIG. 14). At the same time the average life expectancy of test groups were statistically-valid higher (p>0.001) than in control ones. Therefore obtained experimental data prove that the claimed pharmaceutical composition has the effect of modulating of immune system reactions.

C. The Tolerogenic Effect of Pharmaceutical Composition

Test groups of (CBAxC57Bl/6)FI mice were immunized i.p. with pharmaceutical compositions containing 2-acLPS *S. enterica* sv *typhi* O:901 or 3-acLPS *S. enterica* sv *typhi* O:901, or combination of (2-acLPS+3-acLPS+4-acLPS) at mass ratio 1:1:1 *S. enterica* sv *typhi* O:901, at a dose of 50, 100 and 200 mcg/mouse, respectively (that are equivalent to 2.5; 5 and 10 mg/kg) in 0.5 mL of 0.9% sodium chloride (saline solution) prior 72 hours to injection of standard endotoxin-LPS *E. coli* O:55 (Sigma-Aldrich, CLL1A) at a dose of 2 mg/mouse (that is equivalent to 100 mg/kg), that is LD100. Control group of mice was injected i.p. 0.5 mL of saline by the same scheme.

TNF-α amount was determined in mouse blood sera with test-system Quantikine Mouse TNF-α/TNFSF1A (R&D Systems, USA) by ELISA method according to manufacturer's standard protocol. Blood was taken from animals after 90 minutes after endotoxic shock induction. Test results are presented in Table 13.

TABLE 13

The TNF-α production in mice after pre-administration of the claimed pharmaceutical composition performed 72 hours before endotoxic shock induction

| Preparation | Dose, mcg/mouse | TNF-α, (pg/mL) |
|---|---|---|
| Pharmaceutical composition containing 2-acLPS *S. enterica* sv typhi O:901 | 50 | 488 |
| | 100 | 475 |
| | 200 | 468 |
| Pharmaceutical composition containing 3-acLPS *S. enterica* sv typhi O:901 | 50 | 483 |
| | 100 | 413 |
| | 200 | 374 |
| Pharmaceutical composition containing combination of *S. enterica* sv typhi O:901 (2-acLPS + 3-acLPS + 4-acLPS) in mass ratio 1:1:1 | 50 | 493 |
| | 100 | 448 |
| | 200 | 397 |
| Control | 0 | 915 |

Pre-administration of mice with the claimed pharmaceutical composition provided the reduction of in vivo TNF-α production by macrophage to a level below 500 pg/mL while in control group the same level was more than 900 pg/mL (Table 13). Dose-dependent suppression of TNF-α production under immunization with the claimed pharmaceutical compositions proves their tolerogenic effect, which can be used for the correction of various pathological states associated with hyperproduction of proinflammatory cytokines.

Example 5

Preparation and Characterization of Individual Modified S-LPS of Endotoxic Bacteria and their Combinations Thereof A. Isolation and Purification of LPS

*S. flexneri* 2a bacterial culture was obtained by cultivation in 50 liter fermenter. Separation of bacterial cell from liquid phase was performed by flow-through centrifuge. Obtained wet cells were rinsed with saline solution, then with water and lyophilized afterwards.

20 g of dry bacterial cells were extracted by Westphal method (Westphal O., Luderitz O. Chemische Erforschung von Lipopolysacchariden Gram negativer Bakterien. Angew. Chemie., 1954, vol. 66, pp. 407-17), incorporated herein by reference for the purpose stated, by treatment with hot aqueous 45% phenol at 68-70° C.; 960 mg of raw LPS was obtained from water layer following up the dialysis and lyophilization, then dissolved in 0.05 M TRIS-buffer solution, pH=7.2, containing 0.01% $CaCl_2$ and $MgCl_2$, RNA-ase and DNA-ase were added in amount of 100 mg/ml and 10 mg/ml, respectively. After 16 hours of stirring at 37° C., the reaction mixture was treated with 20 mg/mL of Proteinase K for 2 hours at 55° C. Obtained solution was dialyzed using Vladisart ultrafiltration plant with membrane passage limit of 50 kDa.

The solution concentrated after dialysis was lyophilized and 530 mg of pure LPS was prepared containing no more than 2.0% by weight of the proteins, determined by Bradford method (Bradford M. M. A rapid and sensitive method for the quantitation of microgram quantities of protein utilizing the principle of protein-dye binding. Anal. Biochem., 1976, vol. 72, pp. 248-54), and no more than 2.0% by weight of the nucleic acids, determined by Spirin method (Spirin A. S. Spectrophotometric determination of the total content of nucleic acids. Biochemistry (Russian edition), 1958, v. 23, No 4, p. 656).

Obtained LPS was characterized by SDS-PAGE electrophoresis data which demonstrated "classic" pattern of properly alternating bands each of them corresponded to S-LPS molecule with a certain number of repeating units in O-specific polysaccharide chain, where the fastest migrated (the lowest) zone corresponded to R-LPS (FIG. 3 1A).

B. LPS Fractionation by Gel-Chromatography Using Buffer Solution with Sodium Deoxycholate (DOC).

The isolation of S-LPS was carried out with preparative column gel-chromatography in buffer containing 0.25% of DOC as demicellized agent according to procedure described earlier (Peterson, A. A., and McGroarty, E. J., 1985, High-molecular-weight components in lipopolysaccharides of *Salmonella typhimurium*, *Salmonella Minnesota*, and *Escherichia coli*. J. Bacteriol. 162:738-745). Slight modifications of the procedure were concerned the using of Sephadex G-150 instead of Sephadex G-200 due to it's better mechanical characteristics; also a replacement of sodium chloride to sodium acetate in chromatographic buffer for isolation convenience (see below) and a way of apply the LPS solution on the column. Chromatography was performed with using glass column (5×100 cm) at flow elution rate of 1 ml/min and detection with wavelength monitor at 226 nm. Fractions (30 min) eluting near column void volume and containing S-LPS were combined. Removal of chromatographic buffer carried out by dialysis as per Peterson, A. A., and McGroarty procedure and was accompanied by the loss of LPS. That is why fractions containing S-LPS were subjected to lyophilization and obtained dry residue was shaken with ethanol (50-100 mL). S-LPS precipitate was separated by centrifugation and rinsed twice with ethanol. This allowed almost complete discharge of S-LPS product from all buffer components DOC, NaN3, TRIS, EDTA and AcONa soluble in ethanol (as distinguished from sodium chloride because it is soluble in ethanol). The residue was dried in vacuum and the aqueous solution was freeze-dried. The yield of S-LPS was 20-65%. The initial LPS and S-LPS obtained from it were characterized and compared by SDS-PAGE electrophoresis and HPLC. The typical electrophoresis picture of LPS has shown two set of bands. The one was on the bottom of plate corresponding to high-molecular weight substance, the other one was near the front line corresponding to low-molecular compound. The electrophoresis picture of S-LPS has shown only one set of bands corresponding to high-molecular fraction. Bands corresponding to low-molecular weight LPS, including SR- and R-LPS were absent. Thus, highly endotoxic R-LPS were not present in S-LPS preparation. Comparative analysis of the native LPS and S-LPS obtained from it has shown similar set of bands corresponding to high molecular compounds by SDS-PAGE data. After removal the lipid A (2% AcOH, 100° C., 2 hours) the carbohydrate fractions obtained as well from the native LPS as from S-LPS were characterized by HPLC (TSK gel G3000PW 7.8 mm I.D.×30 cm, dist. water, flow rate 1.0 ml/min, dextran calibration). There was no significant amount of low molecular weight compounds on the chromatogram of carbohydrate fraction obtained from S-LPS after hydrolysis. 13C NMR spectrum of S-LPS was identical to the spectrum of O-specific polysaccharide from the initial LPS after cleavage of lipid A and gel-chromatography on Sephadex G-50 column; except for the presence of signals at—=30-34 ppm represents the corresponding carbon atoms of fatty acid residue in S-LPS spectrum. There were no signals of DOC in 13C and 1H NMR spectra (Campredon, M., Quiroa, V., Thevand, A., Allouche, A., & Pouzard, G. (1986). NMR studies of bile acid salts: 2D NMR studies of aqueous and methanolic solutions of sodium cholate and deoxycholate. Magnetic resonance in chemistry, 24(7), 624-629.), that proved the high purity of S-LPS.

C. Preparation of Modified S-LPS (m-S-LPS)

It has followed from the data of the preliminary experiments that search of optimal conditions of alkali hydrolysis was much more complicated for the preparation of m-S-LPS mainly comprising three or four fatty acid residues in the lipid A composition due to the formation of the strong micelles of LPS. In this regard if possible, it is desirable to have demicellated LPS for the realization of the selective saponification because all LPS molecules should be altogether subjected to hydrolysis, i.e it becomes necessary to conduct the reaction in the presence of detergent. Sodium deoxycholate (DOC) was used for this purpose.

Fatty acid profile of lipid A of the obtained m-S-LPS was determined on the basis of mass spectrometry data.

300 mg of S. flexneri 2a S-LPS and 100 mg of DOC were dissolved in 100 mL of diluted solution of ammonium hydroxide ($NH_4OH$ (conc)—$H_2O$=1:2), the solution was stirring for 8 hours at 30° C., diluted with 200 mL of water and neutralized by glacial AcOH on cooling and then lyophilized. 200 mL of ethanol was added to the obtained residue, intensively shaken, centrifuged (20 min, 3800 rpm), the residue was rinsed twice with 200 mL of ethanol, dried in vacuum, dissolved in water and the solution was freeze-dried. The yield of S. flexneri 2a m-S-LPS was 213 mg. The product was characterized similar to S. flexneri 2a S-LPS as described above. m-S-LPS was the major component of the mixture resulting in alkaline hydrolysis, two residues of O-hydroxymyristic acid and one residue of dodecanoic acid were in the lipid A composition (3-acLPS) (m/z 1053.66).

The alkali saponification reaction temperature was raised up to 60° C., more concentrated solution of ammonium hydroxide was used (1:1) and reaction time was increased to 16 hours to obtain m-S-LPS with only two residues of O-hydroxymyristic acid in the lipid A composition (2-acLPS) (m/z 871.5).

The more diluted solution of ammonium hydroxide (1:3) was used for 6 hours at 30° C to obtain m-S-LPS with three residues of O-hydroxymyristic acid and one residue of dodecanoic acid in the lipid A composition (4-acLPS) (m/z1279. 86).

Obviously, the possibility to obtain target 2-acyl LPS, 3-acyl LPS, 4-acyl LPS under proposed approach can be realized as a result of using high-molecular weight S-LPS and thorough selection of conditions. Complete decontamination of S-LPS from R-LPS admixture was initially decreased the endotoxic potential of S-LPS. Careful isolation of S-LPS from R-LPS compound significantly decrease content of lipid A in preparation of S-LPS subjected to modification in comparing with ordinary LPS. Thus, saponification reaction of S-LPS, especially in demicellation conditions, became more manageable in comparing with saponification of LPS under ordinary parameters. Proposed reaction conditions provide deacylation of more acylated lipids A forms (5-acyl LPS, 6-acyl LPS) which could not be detected on modified S-LPS spectra.

The invention claimed is:

1. A composition comprising isolated modified lipopolysaccharide (S-LPS) of endotoxic bacteria comprising: O-specific polysaccharide consisting of one or more repeating units, core oligosaccharide and fully O-deacylated lipid A consisting of two acyl residues, which is free of lipopolysaccharides containing lipid A having five acyl residues or six acyl residues.

2. The composition of claim 1, wherein the composition substantially comprises the isolated modified lipopolysaccharide.

3. The composition of claim 2, which is at least 85% pure.

4. The composition comprising the modified lipopolysaccharide of claim 1, which is a lipopolysaccharide of endotoxic bacteria selected from the group consisting of Salmonella, Escherichia, Shigella, Bordetella, Haemophilus, Campylobacter, Vibrio, Klebsiella, Chlamydia and combinations thereof.

5. A composition comprising isolated modified lipopolysaccharide (S-LPS) of endotoxic bacteria comprising: O-specific polysaccharide consisting of one or more repeating units, core oligosaccharide and partially O-deacylated lipid A consisting of three acyl residues, wherein said modified lipopolysaccharide is free of lipopolysaccharides containing lipid A having five acyl residues or six acyl residues.

6. The composition of claim 5 wherein the composition substantially comprises the isolated modified lipopolysaccharide.

7. The composition of claim 6 which is at least 80% pure.

8. The composition comprising the modified lipopolysaccharide of claim 5, which is a lipopolysaccharide of endotoxic bacteria selected from the group consisting of *Salmonella, Escherichia, Shigella, Bordetella, Haemophilus, Campylobacter, Vibrio, Klebsiella, Chlamydia* and combinations thereof.

9. A composition comprising isolated modified lipopolysaccharide (S-LPS) of endotoxic bacteria comprising: O-specific polysaccharide consisting of one or more repeating units, core oligosaccharide and partially O-deacylated lipid A consisting of four acyl residues, wherein said modified lipopolysaccharide is free of lipopolysaccharides containing lipid A having five acyl residues or six acyl residues.

10. The composition of claim 9, wherein the composition substantially comprises the isolated modified lipopolysaccharide.

11. The composition of claim 10, which is at least 80% pure.

12. The composition comprising the modified lipopolysaccharide of claim 9, which is a lipopolysaccharide of endotoxic bacteria selected from the group consisting of *Salmonella, Escherichia, Shigella, Bordetella, Haemophilus, Campylobacter, Vibrio, Klebsiella, Chlamydia* and combinations thereof.

13. A combination of the modified lipopolysaccharides that comprises (a) a modified lipopolysaccharide (S-LPS) of endotoxic bacteria comprising: O-specific polysaccharide consisting of one or more repeating units, core oligosaccharide and fully O-deacylated lipid A consisting of two acyl residues, and (b) a modified lipopolysaccharide (S-LPS) of endotoxic bacteria comprising: O-specific polysaccharide consisting of one or more repeating units, core oligosaccharide and partially O-deacylated lipid A consisting of three acyl residues, wherein the combination is free of lipopolysaccharides containing lipid A having five acyl residues or six acyl residues.

14. The combination of claim 13, wherein the modified lipopolysaccharides are lipopolysaccharides of endotoxic bacteria selected from the group consisting of *Salmonella, Escherichia, Shigella, Bordetella, Haemophilus, Campylobacter, Vibrio, Klebsiella, Chlamydia* and combinations thereof.

15. The combination of claim 13, further comprising the modified lipopolysaccharide (S-LPS) of endotoxic bacteria that comprises: O-specific polysaccharide consisting of one or more repeating units, core oligosaccharide and partially O-deacylated lipid A consisting of four acyl residues.

16. The combination of claim 15, wherein the modified lipopolysaccharides are lipopolysaccharides of endotoxic bacteria selected from the group consisting of *Salmonella, Escherichia, Shigella, Bordetella, Haemophilus, Campylobacter, Vibrio, Klebsiella, Chlamydia* and combinations thereof.

17. A combination of modified lipopolysaccharides comprising (a) a modified lipopolysaccharide (S-LPS) of endotoxic bacteria, comprising: O-specific polysaccharide consisting of one or more repeating units, core oligosaccharide and fully O-deacylated lipid A consisting of two acyl residues, and (b) a modified lipopolysaccharide (S-LPS) of endotoxic bacteria, comprising: O-specific polysaccharide consisting of one or more repeating units, core oligosaccharide and partially O-deacylated lipid A consisting of four acyl residues, wherein the combination is free of lipopolysaccharides containing lipid A having five acyl residues or six acyl residues.

18. The combination of claim 17, wherein the modified lipopolysaccharides are lipopolysaccharides of endotoxic bacteria selected from the group consisting of *Salmonella, Escherichia, Shigella, Bordetella, Haemophilus, Campylobacter, Vibrio, Klebsiella, Chlamydia* and combinations thereof.

19. A combination of the modified lipopolysaccharides that comprises (a) a modified lipopolysaccharide (S-LPS) of endotoxic bacteria, comprising: O-specific polysaccharide consisting of one or more repeating units, core oligosaccharide and partially O-deacylated lipid A consisting of three acyl residues, and (b) a modified lipopolysaccharide (S-LPS) of endotoxic bacteria, comprising: O-specific polysaccharide consisting of one or more repeating units, core oligosaccharide and partially O-deacylated lipid A consisting of four acyl residues, wherein the combination is free of lipopolysaccharides containing lipid A having five acyl residues or six acyl residues.

20. The combination of claim 19, wherein the modified lipopolysaccharides are lipopolysaccharides of endotoxic bacteria selected from the group consisting of *Salmonella, Escherichia, Shigella, Bordetella, Haemophilus, Campylobacter, Vibrio, Klebsiella, Chlamydia Corynebacterium* and combinations thereof.

21. A vaccine comprising an effective amount of (i) a modified lipopolysaccharide (S-LPS) of endotoxic bacteria comprising: O-specific polysaccharide consisting of one or more repeating units, core oligosaccharide and fully O-deacylated lipid A consisting of two acyl residues, or (ii) a modified lipopolysaccharide (S-LPS) of endotoxic bacteria comprising: O-specific polysaccharide consisting of one or more repeating units, core oligosaccharide and partially O-deacylated lipid A consisting of three acyl residues, or (iii) a modified lipopolysaccharide (S-LPS) of endotoxic bacteria, comprising: O-specific polysaccharide consisting of one or more repeating units, core oligosaccharide and partially O-deacylated lipid A consisting of four acyl residues, or (iv) a combination of modified lipopolysaccharides (i) and (ii), or (v) a combination of modified lipopolysaccharides (i) and (iii), or (vi) a combination of modified lipopolysaccharides (ii) and (iii), or (vii) a combination of modified lipopolysaccharides (i), (ii) and (iii), wherein the vaccine is free of lipopolysaccharides containing lipid A having five acyl residues or six acyl residues.

22. The vaccine of claim 21, wherein the modified lipopolysaccharide is a lipopolysaccharide of endotoxic bacteria selected from the group consisting of *Salmonella, Escherichia, Shigella, Bordetella, Haemophilus, Campylobacter, Vibrio, Klebsiella, Chlamydia* and combinations thereof.

23. The vaccine of claim 21, further comprising at least one pharmaceutically acceptable additive.

24. The vaccine of claim 23, wherein the pharmaceutically acceptable additive is selected from the group consisting of pH stabilizers, preservatives, adjuvants, isotonizing agents and combinations thereof.

25. The vaccine of claim 21, comprising the modified lipopolysaccharide in non-conjugated form.

26. The vaccine of claim 23, wherein said pharmaceutically acceptable additive is a protein carrier.

27. The vaccine of claim 26, wherein said carrier protein is selected from the group consisting of diphtherial anatoxin, tetanus toxoid and *Pseudomonas aeruginosa* exoprotein A.

28. The vaccine of claim 21, comprising the modified lipopolysaccharide in conjugated form.

29. A pharmaceutical composition comprising an effective amount of (i) a modified lipopolysaccharide (S-LPS) of endotoxic bacteria comprising: O-specific polysaccharide consisting of one or more repeating units, core oligosaccharide and fully O-deacylated lipid A consisting of two acyl residues, or (ii) a modified lipopolysaccharide (S-LPS) of endotoxic bacteria comprising: O-specific polysaccharide consisting of one or more repeating units, core oligosaccharide and partially O-deacylated lipid A consisting of three acyl residues, or (iii) a modified lipopolysaccharide (S-LPS) of endotoxic bacteria comprising: O-specific polysaccharide consisting of one or more repeating units, core oligosaccharide and partially O-deacylated lipid A consisting of four acyl residues, or (iv) a combination of modified lipopolysaccharides (i) and (ii), or (v) a combination of modified lipopolysaccharides (i) and (iii), or (vi) a combination of modified lipopolysaccharides (ii) and (iii), or (vii) a combination of modified lipopolysaccharides (i), (ii) and (iii), wherein the pharmaceutical composition is free of lipopolysaccharides containing lipid A having five acyl residues or six acyl residues.

30. The pharmaceutical composition of claim 29, wherein the modified lipopolysaccharide is a lipopolysaccharide of endotoxic bacteria selected from the group consisting of *Salmonella, Escherichia, Shigella, Bordetella, Haemophilus, Campylobacter, Vibrio, Klebsiella, Chlamydia* and combinations thereof.

31. The pharmaceutical composition of claim 29, further comprising at least one pharmaceutically acceptable additive.

32. The pharmaceutical composition of claim 31, wherein the pharmaceutically acceptable additive is selected from the group consisting of preservatives, stabilizers, solvents and combinations thereof.

33. A method of prophylaxis of infectious diseases caused by gram negative bacteria comprising administering a prophylactically effective amount of the vaccine of claim 21 to a patient in need thereof.

34. The method of claim 33, further comprising repeating administration of said vaccine to cause a secondary immune reaction.

35. The method of claim 33, wherein said vaccine comprises modified lipopolysaccharide of endotoxic bacteria selected from the group consisting of *Salmonella, Escherichia, Shigella, Bordetella, Haemophilus, Campylobacter, Vibrio, Klebsiella, Chlamydia* and combinations thereof.

36. A method of prophylaxis of endotoxic shock or septic shock comprising administering a prophylactically effective amount of (i) a modified lipopolysaccharide (S-LPS) of endotoxic bacteria, comprising: O-specific polysaccharide consisting of one or more repeating units, core oligosaccharide and fully O-deacylated lipid A consisting of two acyl residues, or (ii) a modified lipopolysaccharide (S-LPS) of endotoxic bacteria comprising: O-specific polysaccharide consisting of one or more repeating units, core oligosaccharide and partially O-deacylated lipid A consisting of three acyl residues, or (iii) a modified lipopolysaccharide (S-LPS) of endotoxic bacteria, comprising: O-specific polysaccharide consisting of one or more repeating units, core oligosaccharide and partially O-deacylated lipid A consisting of four acyl residues, or (iv) a combination of modified lipopolysaccharides (i) and (ii), or (v) a combination of modified lipopolysaccharides i) and iii), or vi) a combination of modified lipopolysaccharides (ii) and (iii), or (vii) a combination of modified lipopolysaccharides (i), (ii) and (iii), wherein any of said modified lipopolysaccharide or any of said combinations is free of lipopolysaccharides containing lipid A having five acyl residues or six acyl residues.

37. The method of claim 36, wherein any of said modified lipopolysaccharide is a modified lipopolysaccharide of endotoxic bacteria selected from the group consisting of *Salmonella, Escherichia, Shigella, Bordetella, Haemophilus, Campylobacter, Vibrio, Klebsiella, Chlamydia* and combinations thereof.

38. A method of treating endotoxic shock or septic shock comprising administering a therapeutically effective amount of (i) a modified lipopolysaccharide (S-LPS) of endotoxic bacteria, comprising: O-specific polysaccharide consisting of one or more repeating units, core oligosaccharide and fully O-deacylated lipid A consisting of two acyl residues, or (ii) a modified lipopolysaccharide (S-LPS) of endotoxic bacteria, comprising: O-specific polysaccharide consisting of one or more repeating units, core oligosaccharide and partially O-deacylated lipid A consisting of three acyl residues, or (iii) a modified lipopolysaccharide (S-LPS) of endotoxic bacteria, comprising: O-specific polysaccharide consisting of one or more repeating units, core oligosaccharide and partially O-deacylated lipid A consisting of four acyl residues, or (iv) a combination of modified lipopolysaccharides (i) and (ii), or (v) a combination of modified lipopolysaccharides (i) and (iii), or (vi) a combination of modified lipopolysaccharides (ii) and (iii), or (vii) a combination of modified lipopolysaccharides (i), (ii) and (iii) to a patient in need thereof, wherein any of said modified lipopolysaccharide or any of said combinations is free of lipopolysaccharides containing lipid A having five acyl residues or six acyl residues.

39. The method of claim 38, wherein any of said modified lipopolysaccharides is a modified lipopolysaccharide of endotoxic bacteria selected from the group consisting of *Salmonella, Escherichia, Shigella, Bordetella, Haemophilus, Campylobacter, Vibrio, Klebsiella, Chlamydia* and combinations thereof.

40. A method of treating influenza comprising administering the pharmaceutical composition of claim 29 to a patient in need thereof.

41. The method of claim 40, wherein said influenza is H1N1.

42. The method of claim 40, wherein said pharmaceutical composition comprises the combination of modified lipopolysaccharides (i), (ii) and (iii).

43. The method of claim 42, wherein said modified lipopolysaccharides are present in the ratio of 1:1:1.

44. The method of claim 40, wherein said pharmaceutical composition comprises modified lipopolysaccharides of *Salmonella*.

45. The modified lipopolysaccharide of claim 1 or claim 5, or claim 9, which is an immunostimulating carrier in the manufacture of a vaccine.

46. The modified lipopolysaccharide of claim 45, which is lipopolysaccharide of endotoxic bacteria selected from the group consisting of *Salmonella, Escherichia, Shigella, Bordetella, Haemophilus, Campylobacter, Vibrio, Klebsiella, Chlamydia* and combinations thereof.

47. The modified lipopolysaccharide of claim 45, which is apyrogenic for rabbits in a dose of up to 100 mcg/kg in rabbit pyrogenicity test.

48. The modified lipopolysaccharide of claim 45, which is conjugated with a protective antigen or hapten.

49. The modified lipopolysaccharide of claim 48, wherein the protective antigen is selected from the group consisting of synthetic, protein and polysaccharide antigens.

50. The modified lipopolysaccharide of claim 48, wherein the hapten is selected from the group consisting of protein and polysaccharide haptens.

51. The modified lipopolysaccharide of claim 45, wherein the vaccine is selected from the group consisting of vaccine for the bacterial infection prophylaxis and vaccine for the viral infection prophylaxis.

52. The combination of the modified lipopolysaccharides of claim 13 or claim 15, or claim 17, which is an immunostimulating carrier in the manufacture of a vaccine.

53. The combination of modified lipopolysaccharides of claim 52, which are lipopolysaccharides of endotoxic bacteria selected from the group consisting of *Salmonella, Escherichia, Shigella, Bordetella, Haemophilus, Campylobacter, Vibrio, Klebsiella, Chlamydia* and combinations thereof.

54. The combination of modified lipopolysaccharides of claim 52, which is apyrogenic for rabbits in a dose of up to 100 mcg/kg in rabbit pyrogenicity test.

55. The combination of modified lipopolysaccharides of claim 52, wherein the modified lipopolysaccharides are conjugated with a protective antigen or hapten.

56. The combination of modified lipopolysaccharides of claim 55, wherein the protective antigen is selected from the group consisting of protein and polysaccharide antigens.

57. The combination of modified lipopolysaccharides of claim 55, wherein the hapten is selected from the group consisting of protein and polysaccharide haptens.

58. The combination of modified lipopolysaccharides of claim 52, wherein the vaccine is selected from the group consisting of vaccine for the bacterial infection prophylaxis and vaccine for the viral infection prophylaxis.

* * * * *